United States Patent [19]

Tanaka et al.

[11] Patent Number: 5,476,602
[45] Date of Patent: * Dec. 19, 1995

[54] POLYCARBONATES, USES THEREOF, PROCESSES FOR PREPARING AND PURIFYING SAME

[75] Inventors: Masahide Tanaka; Tadaaki Fujimoto; Tetsuo Hayashi; Takashi Hayashi; Kazunori Takahata, all of Yamaguchi, Japan

[73] Assignee: Mitsui Petrochemical Industries, Ltd., Tokyo, Japan

[ * ] Notice: The portion of the term of this patent subsequent to Mar. 15, 2011, has been disclaimed.

[21] Appl. No.: 170,809

[22] Filed: Dec. 21, 1993

Related U.S. Application Data

[63] Continuation-in-part of Ser. No. 856,956, May 14, 1992, Pat. No. 5,294,356.

[30] Foreign Application Priority Data

| Sep. 17, 1990 | [JP] | Japan | 2-246891 |
| Sep. 27, 1990 | [JP] | Japan | 2-258179 |
| Sep. 28, 1990 | [JP] | Japan | 2-261271 |
| Oct. 2, 1990 | [JP] | Japan | 2-265528 |
| Feb. 22, 1991 | [JP] | Japan | 3-28933 |
| Aug. 5, 1991 | [JP] | Japan | 3-195557 |
| Sep. 6, 1993 | [JP] | Japan | 5-220808 |

[51] Int. Cl.$^6$ .............. C10M 105/36; C10M 105/32
[52] U.S. Cl. .............. 252/56 R; 252/52 A; 252/68
[58] Field of Search .............. 252/56 R, 52 A, 252/68

[56] References Cited

U.S. PATENT DOCUMENTS

| 2,379,249 | 6/1945 | Muskat | 558/265 |
| 2,384,123 | 9/1945 | Muskat et al. | 558/265 |
| 2,789,968 | 4/1957 | Reynolds et al. | 558/265 |
| 2,844,451 | 7/1958 | Alpert et al. | 558/266 |
| 2,866,757 | 12/1958 | Newman et al. | 252/56 R |
| 3,497,478 | 2/1970 | Field | 558/265 |
| 4,217,298 | 8/1980 | Shikata et al. | 558/265 |
| 4,273,726 | 6/1981 | Altuglu | 558/265 |
| 4,293,503 | 10/1981 | Young | 558/265 |
| 5,114,605 | 5/1992 | Mizui et al. | 252/56 R |
| 5,238,590 | 8/1993 | Mizui et al. | 252/52 A |
| 5,262,076 | 11/1993 | Ishida et al. | 252/52 A |
| 5,294,356 | 3/1994 | Tanaka et al. | 252/56 R |
| 5,326,486 | 7/1994 | Mizui et al. | 252/56 R |
| 5,370,809 | 12/1994 | Ishida et al. | 252/52 A |
| 5,384,056 | 1/1995 | Tanaka et al. | 252/56 R |
| 5,387,354 | 2/1995 | Mizui et al. | 252/56 R |

FOREIGN PATENT DOCUMENTS

| 1367493 | 4/1964 | France . |
| 1006565 | 4/1957 | Germany . |
| 2110234 | 6/1983 | United Kingdom . |

*Primary Examiner*—Jerry D. Johnson
*Attorney, Agent, or Firm*—Sherman and Shalloway

[57] ABSTRACT

The polycarbonates of the present invention include those of sucrose series having a specific cyclic structure, those of oligosaccharide and monosaccharide series other than the sucrose series, those derived from specific saccharides having no cyclic structure, those having a skeletal structure of pentaerythritol, neopentyl glycol or trimethylolmethane, and specific dicarbonates.

The lubricating oil and electrical insulating oil of the invention contain the above-mentioned polycarbonates.

The polycarbonates of tile invention are excellent in compatibility with Freon R-134a (HFC) as well as in lubricating properties, detergency and electrical insulating properties, and are capable of providing lubricating oil for refrigerator, automotive engine oil, automotive gear oil, lubricating oil for rolling and lubricating oil for fiber, especially lubricating oil for which electrical insulating properties are required, and electrical insulating oil.

12 Claims, 5 Drawing Sheets

POLYCARBONATES, USES THEREOF, PROCESSES FOR PREPARING AND PURIFYING SAME

This is a continuation-in-part of application Ser. No. 07/856,956 filed May 14, 1992, which issued on Mar. 15, 1994 as U.S. Pat. No. 5,294,356. The application Ser. No. 07/856,956 is incorporated herein in its entirety by reference thereto.

TECHNICAL FIELD

The present invention relates to novel polycarbonates and uses thereof, more particularly to polycarbonates which are excellent in compatibility with hydrogenated fluorocarbon (HFC) used as a refrigerant for refrigerators such as Freon R-134a or R-152a which is nondestructive to the ozone layer, hydrogenated chlorofluorocarbon (HCFC) which is small in ozone depletion potential such as Freon R-22, R-123 or R-124, and mixtures of the above-mentioned hydrogenated products and also excellent in lubricating properties. This invention also relates to lubricant oil comprising such polycarbonates as mentioned above, particularly those suitable for use in refrigerators where Freon which is nondestructive to the ozone layer is used as a refrigerant.

Further, the present invention relates to polycarbonates excellent in compatibility and lubricating properties as aforesaid and also excellent in electrical insulation properties, and to lubricant oil and electrical insulating oil comprising such polycarbonates as mentioned above, particularly lubricant oil suitable for use in refrigerators where Freon which is nondestructive to the ozone layer is used as a refrigerant, and lubricant oil and electrical insulating oil suitable for use in electric refrigerators.

Furthermore, the present invention relates to processes for preparing and purifying the polycarbonates as mentioned above.

TECHNOLOGICAL BACKGROUND

With the alteration of refrigerant gas for refrigerators to hydrogenated fluorocarbons such as Freon R-134a ($CH_2F-CF_3$) which is an ozone layer-nondestructive HFC, mineral oils or alkylbenzenes which have heretofore been used as lubricant oil for refrigerators have come not to be used therefor because they have no compatibility with the refrigerant gas. Accordingly, such compounds as polypropylene glycol, polypropylene glycol monoalkyl ether and polypropylene glycol dialkyl ether have come to be used as lubricant oil for refrigerators. However, the above-mentioned compounds are low in compatibility with Freon R-134a, and there was such a problem that among the compounds mentioned above, those having such high viscosity as a kinematic viscosity at 100° C. of more than 15 cSt are particularly low in compatibility with Freon 134a, and hence exhibit low performance as a lubricant oil for refrigerators, for example, a lubricant oil for a rotary automatic air-conditioner.

By the way, polycarbonates are materials which are usable as various lubricant oils or components thereof. However, polycarbonates known heretofore have a volume resistivity of the order of $10^{11}$ to $10^{12}$ Ω.cm, and they were not always sufficient to show good electrical insulation properties when used in the fields of lubricant oils and electrical insulating oils where the electrical insulation properties are required.

Accordingly, there has heretofore been desired not only the advent of highly viscous compounds excellent in lubricating properties as well as electrical insulating properties and also in compatibility with Freon R-134a but also the advent of lubricant oils for refrigerators containing such compounds as mentioned above.

French Patent No. 2,321,477 discloses tricarbonate of trimethylolpropane represented by the following general formula.

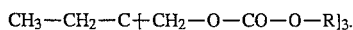

$CH_3-CH_2-C+CH_2-O-CO-O-R]_3$.

In the above general formula, R is branched or non-branched alkyl of 4–12 carbon atoms, cycloalkyl, allyl or aralkyl which may be substituted sometimes with lower alkyl. According to the above-cited French patent, it is alleged that the disclosed tricarbonate can be used as a main component of lubricants stable to heat, and the lubricants containing this tricarbonate may be used particularly in supersonic aircraft.

Of the polycarbonates, particularly those having an alkyl group at the molecular terminals have such an advantage that they are low in hygroscopicity. Japanese Patent L-O-P Publn. No. 3865/1971 discloses a process for preparing such polycarbonates. That is, this Japanese publication teaches that such polycarbonates as mentioned above may be obtained by allowing 1 or 2 mols of a diol to react with 1 or 2 mols of a monoalcohol in a mixture of n mols of the diol and (n-1) mols of diphenyl carbonate. For example, the above-cited publication discloses a process for preparing a polycarbonate having a decyl group at the molecular terminals by allowing n-decanol as the above-mentioned diol to react with polyethylene glycol as the above-mentioned diol while heating under a reduced pressure.

In the above-mentioned process, highly reactive diphenyl carbonate is used preferably as a starting carbonate. The reason why highly reactive diphenyl carbonate is used as the starting carbonate in preference to other carbonates is that this diphenyl carbonate has a high boiling point and so it is easy to preset the reaction conditions therefor.

In contrast thereto, when dimethyl carbonate or diethyl carbonate which is low in reactivity and has a low boiling point is used as the starting carbonate in the above-mentioned process, it is not easy to terminate the molecular terminals of the resulting polycarbonate substantially only with an alkyl group. Furthermore, a catalyst must be used when such a low reactive carbonate as mentioned above is used as the starting carbonate, but it is also not easy to remove the catalyst having a high boiling point from the reaction product.

It is, however, industrially economically advantageous to use, as the starting material, dimethyl carbonate or diethyl carbonate which is available at a low price as compared with diphenyl carbonate.

It has already been known, in general, that a polycarbonate can be obtained by a reaction of a monoalcohol to react with a carbonate such as dimethyl carbonate.

However, no desired polycarbonate can be obtained in good yield by the prior art process for preparing polycarbonates by allowing a polyol instead of a monoalcohol to react with the carbonate, distilling off the remaining unreacted carbonate by heating after completion of the reaction, and neutralizing the catalyst with an acid, because polymerization of the above-mentioned unreacted carbonate takes place at the stage of distilling off said unreacted carbonate.

As the process for preparing polycarbonates, there has heretofore been known, for example, a process for preparing polycarbonate which comprises reacting a polyol such as diethylene glycol with a carbonate such as dimethyl carbonate by heating in the presence of a basic catalyst, distilling off the unreacted carbonate by heating, and neutralizing the catalyst with an acid such as an organic acid.

In the polycarbonate obtained by the above-mentioned process where the catalyst contained in said polycarbonate is merely neutralized, however, an ionic compound remains therein. Accordingly, the polycarbonates obtained by the above-mentioned process involve such a problem that their characteristics such as electrical resistance properties will deteriorate.

The present invention is intended to solve such problems associated with the prior art as mentioned above, and an object of the invention is to provide polycarbonates excellent in compatibility with an ozone layer-nondestructive hydrogenated fluorocarbon such as Freon R-134a, with hydrogenated chlorofluorocarbon having small ozone destruction power and further with mixtures thereof, particularly highly viscous polycarbonate excellent in compatibility (mutual solubility) with Freon R-134a.

A further object of the invention is to provide polycarbonates excellent not only in compatibility as aforesaid but also in lubricating properties as well as in electrical insulation properties.

Another object of the invention is to provide lubricant oils and electrical insulating oils comprising the above-mentioned polycarbonates, particularly lubricant oils suited for use in refrigerators where an ozone layer-nondestructive Freon is used as a refrigerant, and lubricant oils and electrical insulating oils particularly suited for use in electric refrigerators.

A still further object of the invention is to provide a process for preparing polycarbonates having an alkyl group at the molecular terminals in high yields and in an economical manner by aid of simplified preparative step.

A still another object of the invention is to provide a process for purifying polycarbonates by removing basic substances from the polycarbonates containing the same and thereby obtaining polycarbonates excellent in electrical insulation properties.

DISCLOSURE OF THE INVENTION

The first novel polycarbonates of the present invention are those represented by the following general formula [I].

$$Su\!-\!O\!-\!R \qquad \ldots [I]$$

wherein Su is a group represented by the following formula (A) and R is a group selected from the groups represented by the following formulas (B), (C), (D), (E) and (F).

(A)

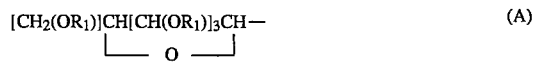
(B)

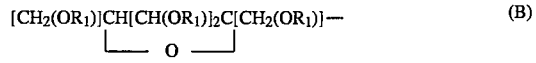
(C)

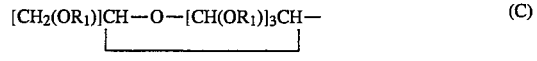
(D)

In the above-mentioned formulas (A), (B), (C) and (D), $R_1$ is a group represented by the following formula (E) or (F).

$$-(C_3H_6O)_n\ COOR_2 \qquad \ldots (E)$$

wherein $R_2$ is each independently a hydrocarbon group having not more than 30 carbon atoms or a hydrocarbon group containing an ether bond and having 2 to 30 carbon atoms, and n is an integer of 1 to 12.

$$-(C_3H_6O)_n\ (C_2H_4O)_p\ COOR_2 \qquad \ldots (F)$$

wherein $R_2$ is as defined in the above-mentioned formula (E), and n and p are each an integer of 1 to 12.

The second novel polycarbonates of the invention are those represented by the following general formula [II].

$$(R_1O)\ CH_2\ [CH(OR_1)]_m\ CH_2\ (OR_1) \qquad \ldots [II]$$

wherein $R_1$ is a group represented by the following formula (E) or (F), and m is an integer of 1 to 6.

$$-(C_3H_6O)_n\ COOR_2 \qquad \ldots (E)$$

wherein $R_2$ and n are as defined above, respectively.

$$-(C_3H_6O)_n\ (C_2H_4O)_p\ COOR_2 \qquad \ldots (F)$$

wherein $R_2$, n and m are as defined above, respectively.

The third novel polycarbonates of the invention are those represented by the following general formula [VIII].

$$(CH_3)_x\ C(CH_2OCOOR_{10})_y \qquad \ldots [III]$$

wherein $R_{10}$ is each independently a hydrocarbon group having not more than 30 carbon atoms or a hydrocarbon group containing an ether bond and having 2 to 30 carbon atoms, x is an integer of 0 to 2, and y is an integer of 2 to 4.

The fourth novel polycarbonates of the invention are those represented by the following general formula [XIII].

$$R_{15}OCOOR_{16}OCOOR_{17} \qquad \ldots [XIII]$$

wherein $R_{15}$ and $R_{17}$ are each independently a hydrocarbon group having not more than 30 carbon atoms or a hydrocarbon group containing an ether bond and having 2 to 30 carbon atoms, and $R_{16}$ is a straight chain or branched hydrocarbon group having carbon atoms totaling to 5 to 8, the main chain of which has 4 to 8 carbon atoms.

The lubricant oils of the present invention, such as those for refrigerators, are characterized by containing the above-mentioned first, second, third or fourth polycarbonates of the invention.

The lubricant oils of the invention are excellent in lubricating properties as well as in detergency, and they are easy to decrease in viscosity at low temperature, hence the present lubricant oils can be used for wide applications such as industrial gear oil, automotive engine oil, automotive gear oil, lubricant oil for refrigerators such as automotive air-conditioner and electric refrigerator, lubricant oil for the textile industry and lubricant oil for the rolling mill.

The present lubricant oils are excellent not only in such characteristics as mentioned above but also excellent in compatibility with an ozone layer-nondestructive Freon such as Freon R-134a or R-152a, with a hydrogenated fluorocarbon having a small ozone destructing force such as Freon R-22, R123 and R-124, and with mixtures thereof, hence they can be used as lubricant oil for refrigerators wherein the abovementioned ozone layer-nondestructive Freon, hydrogenated fluorocarbon and mixture thereof are used as refrigerant.

In the present invention, lubricant oils containing, besides the above-mentioned polycarbonates, an ozone layer-nondestructive Freon such as R-134a, a hydrogenated fluorocarbon having a small ozone destructing force such as Freon R-22 and mixtures thereof may also be used as lubricant oil for refrigerators.

In the present specification, the term "lubricant oil" is intended to include lubricant oils comprising the polycarbonates of the invention and other components and also lubricant oils comprising the polycarbonates of the invention only.

The electrical insulating oils of the present invention are characterized by comprising the above-mentioned third or fourth polycarbonates of the invention.

The process for preparing the polycarbonates of the present invention represented by the general formula [XVIII]:

$$R_{22}(OCOO-R_{23})_l \qquad \ldots [XVIII]$$

(wherein $R_{22}$ is an aliphatic hydrocarbon group of 4 to 300 carbon atoms, an aliphatic hydrocarbon group containing an ether bond and having 4 to 300 carbon atoms or a cyclic hydrocarbon group containing an ether bond and having 6 to 300 carbon atoms, $R_{23}$ is a hydrocarbon group having not more than 30 carbon atoms or a hydrocarbon group containing an ether bond and having 2 to 30 carbon atoms, and l is an integer of 2 to 8), is characterized in that a mixture comprising (a) a polyol represented by the general formula [XIX]:

$$R_{22}(OH)_l \qquad \ldots [XIX]$$

wherein $R_{22}$ and l are the same as $R_{22}$ and l in the abovementioned general formula [XVIII], a monoalcohol represented by the general formula [XX]:

$$R_{23}OH \qquad \ldots [XX]$$

wherein $R_{23}$ is the same as $R_{23}$ in the above-mentioned general formula [XVIII], and (c) a carbonate represented by the general formula [XXI]:

$$R_{24}OCOO R_{24} \qquad \ldots [XXI]$$

wherein $R_{24}$ are each independently an alkyl group having 1 to 2 carbon atoms, $R_{24}OH$ resulting from said carbonate during the course of reaction being lower in boiling point from those of the above-mentioned polyol and monoalcohol, and said carbonate being used in such an amount that a ratio of the number of moles of the carbonate to 1-times the number of moles of the polyol of the above-mentioned general formula [XIXI] being from 2 to 200, is heated in the presence of a basic catalyst, and the mixture is allowed to undergo reaction so as to proceed to a reaction ratio of not less than 95% while distilling off the resulting alcohol ($R_{24}OH$) from the reaction system, the basic catalyst is then removed from the reaction product containing the same, and unaltered carbonate and carbonate which has not participated to the final stage reaction ($R_{25}OCO_2R_{25}$ wherein $R_{25}$ are each independently the above-defined $R_{23}$ or $R_{24}$) are distilled off from the reaction system.

The process for the purifying polycarbonates of the present invention is characterized in that from the polycarbonates as prepared in the presence of a basic catalyst, basic substances contained in said polycarbonates are removed by water washing and/or bringing into contact with an inorganic ion exchanger.

PREFERRED EMBODIMENT OF THE INVENTION

Figure 1:
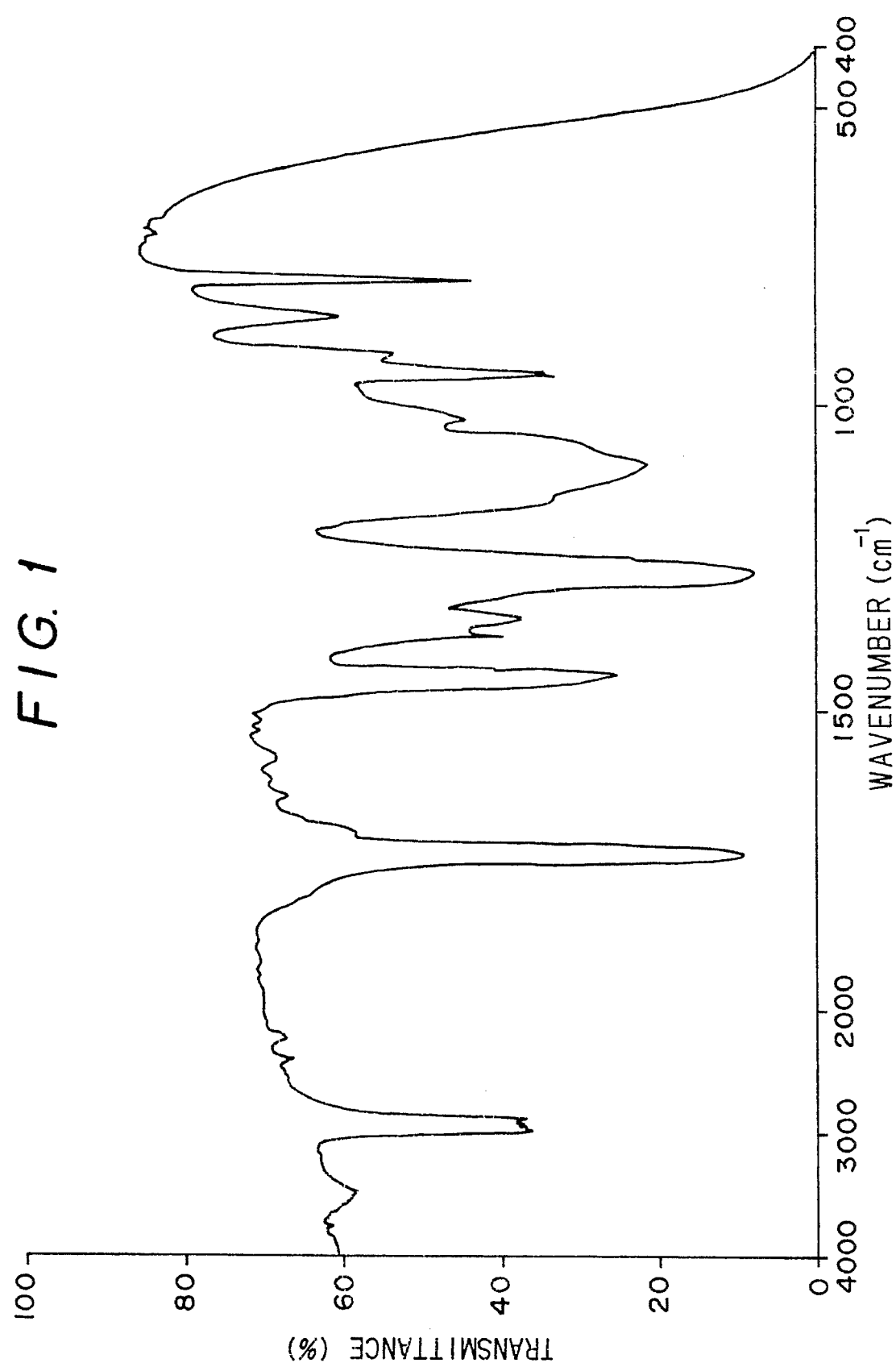
FIGS. 1, 2, 3 and 4 are graphs individually showing IR absorption spectra of polycarbonates obtained in Examples 1, 9, 21 and 25, respectively.

The polycarbonates, uses thereof and processes for preparing and purifying the same according to the present invention are illustrated below in detail.

First of all, the first and second novel polycarbonates of the invention and the uses of the same are described hereinafter.

The first novel polycarbonates of the invention are sucrose polycarbonates, oligosaccharide polycarbonates other than the sucrose polycarbonates and monosaccharide polycarbonates, all being represented by the following general formula [I].

$$Su-O-R \qquad \ldots (I)$$

wherein Su is a group represented by the following formula (A) and R is a group selected from the following formulas (B), (C), (D), (E) and (F).

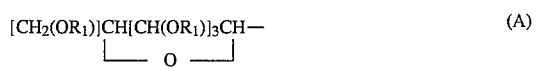  (A)

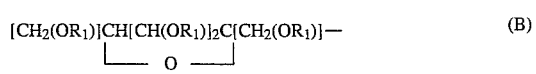  (B)

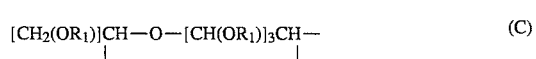  (C)

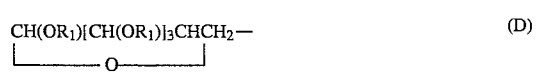  (D)

In the above-mentioned formulas (A), (B), (C) and (D), $R_1$ is a group represented by the following formula (E) or (F).

$$-(C_3H_6O)_n\ COOR_2 \qquad \ldots (E)$$

wherein $R_2$ is each independently a hydrocarbon group having not more than 30 carbon atoms or a hydrocarbon group containing an ether bond and having 2 to 30 carbon atoms, and n is an integer of 1 to 12.

$$-(C_3H_6O)_n\ (C_2H_4O)_p\ COOR_2 \qquad \ldots (F)$$

wherein $R_2$ and n are as defined in the above-mentioned formula (E), and p is an integer of 1 to 12.

The second novel polycarbonates of the invention are those derived from sugar having no cyclic structure and having the following general formula [II].

$$(R_{10})\, CH_2\, [CH(OR_1)]_m\, CH_2\, (OR_1) \quad \ldots [II]$$

wherein $R_1$ is a group represented by the following formula (E) or (F), and m is an integer of 1 to 6.

$$-(C_3H_6O)_n\, COOR_2 \quad \ldots (E)$$

wherein $R_2$ and n are as defined in the above-mentioned formula (E).

$$-(C_3H_6O)_n\, (C_2H_4O)_p\, COOR_2 \quad \ldots (F)$$

wherein $R_2$, n and p are as defined in the above-mentioned formula (F).

In the present invention, the ratio of n to p (n/p) in the above-mentioned formula (F) is 0.5 to 20, preferably 1 to 10 and especially 2 to 5.

In the above-mentioned formulas (E) and (F), the hydrocarbon group as $R_2$ includes aliphatic hydrocarbons, alicyclic hydrocarbons, aromatic hydrocarbons, aromatic aliphatic hydrocarbons and glycol ethers represented by the following general formula $$-(R_3-O)_q-R_4$$

wherein $R_3$ is an alkylene group having 2 to 3 carbon atoms, R4 is a hydrocarbon group having not more than 28 carbon atoms, and q is an integer of 1 to 20.

Concrete examples of the aliphatic hydrocarbon group as the above-mentioned $R_2$ include methyl, ethyl, n-propyl, isopropyl, n-butyl, isobutyl, s-butyl, t-butyl, pentyl, isopentyl, neopentyl, n-hexyl, 2,3-dimethylbutyl, isohexyl, n-heptyl, isoheptyl, n-octyl, 2-ethylhexyl, isooctyl, n-nonyl, isononyl, n-decyl, isodecyl, n-undecyl, isoundecyl, n-dodecyl, isododecyl, n-tridecyl, isotridecyl, n-tetradecyl, isotetradecyl, n-pentadecyl, isopentadecyl, n-hexadecyl, isohexadecyl, n-heptadecyl, isoheptadecyl, n-octadecyl, isooctadecyl, n-nonyldecyl, isononyldecyl, n-eicosanyl, isoeicosanyl, 2-ethylhexyl and 2-(4-methylpentyl).

Further, concrete examples of the alicyclic hydrocarbon group as the above-mentioned $R_2$ include cyclohexyl, 1-cyclohexenyl, methylcyclohexyl, dimethylcyclohexyl, decahydronaphthyl and tricyclodecanyl.

Furthermore, concrete examples of the aromatic hydrocarbon group as the above-mentioned $R_2$ include phenyl, o-tolyl, p-tolyl, m-tolyl, 2,4-xylyl, mesityl and 1-naphthyl.

Still further, concrete examples of the aromatic aliphatic hydrocarbon group as the above-mentioned $R_2$ include benzyl, methylbenzyl, β-phenylethyl (phenetyl), 1-phenylethyl, 1-methyl-1-phenylethyl, p-methylbenzyl, styryl and cinnamyl.

Concrete examples of the alkylene group as the abovementioned $R_3$ include ethylene, propylene and isopropylene.

Further, the hydrocarbon group as the above-mentioned $R_4$ includes aliphatic hydrocarbons, alicyclic hydrocarbons, and aromatic hydrocarbons. Concrete examples of these hydrocarbons mentioned above include the same examples exemplified as the aliphatic hydrocarbons, alicyclic hydrocarbons and aromatic hydrocarbons of the above-mentioned $R_2$.

The glycol ether group represented by the abovementioned general formula $-(R_3-O)_q-R_4$ includes concretely ethylene glycol monomethyl ether, ethylene glycol monobutyl ether, diethylene glycol mono-n-butyl ether, triethylene glycol monoethyl ether, propylene glycol monomethyl ether, propylene glycol monobutyl ether, dipropylene glycol monoethyl ether and tripropylene glycol mono-n-butyl ether.

When the first and second novel polycarbonates of the invention are used as lubricant oils for refrigerators wherein an ozone layer-nondestructive Freon gas such as Freon R-134a is used as a refrigerant, the above-mentioned $R_2$ represents desirably lower alkyl such as methyl, ethyl, isopropyl or n-butyl, or alkylene glycol monoalkyl ether such as ethylene glycol monomethyl ether, ethylene glycol monobutyl ether, diethylene glycol monomethyl ether, triethylene glycol monomethyl ether, propylene glycol monomethyl ether, propylene glycol monobutyl ether, dipropylene glycol monoethyl ether or tripropylene glycol mono-n-butyl ether.

The first novel polycarbonates of the invention represented by the above-mentioned general formula [I] include concretely, for example, those having the following formulas as mentioned below, respectively.

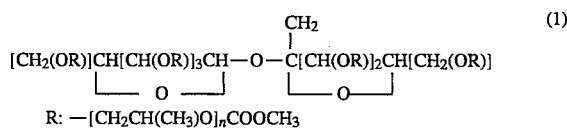 (1)
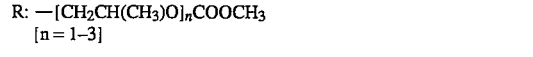

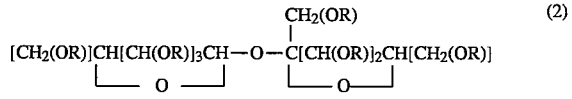 (2)
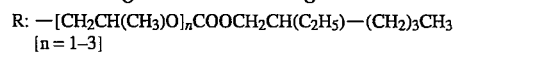

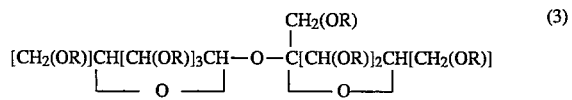 (3)
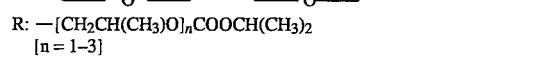

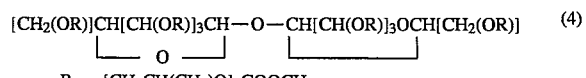 (4)
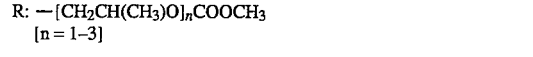

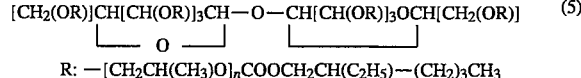 (5)
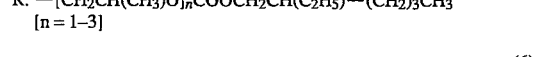

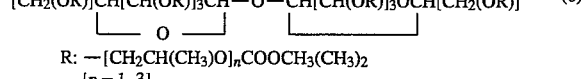 (6)
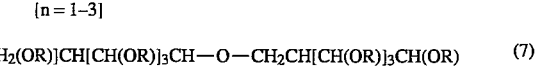

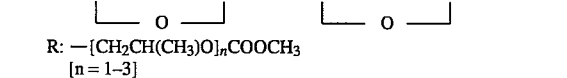 (7)
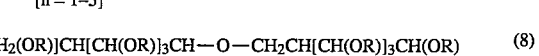

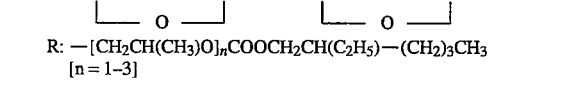 (8)
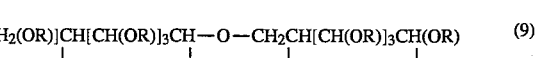

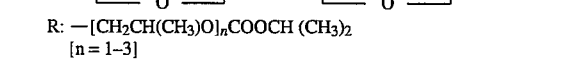 (9)
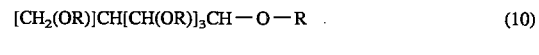

 (10)

-continued

R: —[CH$_2$CH(CH$_3$)O]$_n$COOCH$_3$
[n = 1–3]

[CH$_2$(OR)]CH[CH(OR)]$_3$CH—O—R  (11)
R: —[CH$_2$CH(CH$_3$)O]$_n$COOCH$_2$CH(C$_2$H$_5$)—(CH$_2$)$_3$CH$_3$
[n = 1–3]

[CH$_2$(OR)]CH[CH(OR)]$_3$CH—O—R  (12)
R: —[CH$_2$CH(CH$_3$)O]$_n$COOCH(CH$_3$)$_2$
[n = 1–3]

[CH$_2$(OR)]CH[CH(OR)]$_3$CH—O—R  (13)
R: —[CH$_2$CH(CH$_3$)O]$_n$(C$_2$H$_4$O)COOCH$_3$
[n = 1–3]

[CH$_2$(OR)]CH[CH(OR)]$_3$CH—O—R  (14)
R: —[CH$_2$CH(CH$_3$)O]$_n$(C$_2$H$_4$O)COOCH$_2$CH(C$_2$H$_5$)—(CH$_2$)$_3$CH$_3$
[n = 1–3]

[CH$_2$(OR)]CH[CH(OR)]$_3$CH—O—R  (15)
R: —[CH$_2$CH(CH$_3$)O]$_n$(C$_2$H$_4$O)COOCH(CH$_3$)$_2$
[n = 1–3]

Further, the second novel polycarbonates of the invention represented by the above-mentioned general formula [II] include concretely, for example, those having the following formulas as mentioned below, respectively.

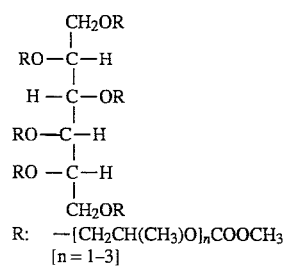  (1)

R: —[CH$_2$CH(CH$_3$)O]$_n$COOCH$_3$
[n = 1–3]

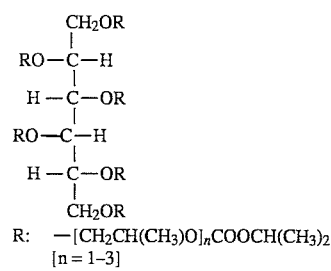  (2)

R: —[CH$_2$CH(CH$_3$)O]$_n$COOCH(CH$_3$)$_2$
[n = 1–3]

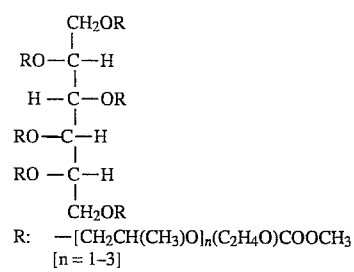  (1)

R: —[CH$_2$CH(CH$_3$)O]$_n$(C$_2$H$_4$O)COOCH$_3$
[n = 1–3]

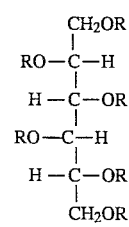  (2)

-continued

R: —[CH$_2$CH(CH$_3$)O]$_n$(C$_2$H$_4$O)COOCH(CH$_3$)$_2$
[n = 1–3]

The polycarbonates represented by the above-mentioned general formula [I] or [II] may be prepared, for example, by a process as mentioned below.

First, a mixture comprising (a) a polyol represented by the general formula [III] or [IV] as will be mentioned later, and (b) a carbonate represented by the general formula [V]:

$$R_5OCOOR_5 \quad \ldots [V]$$

wherein R$_5$ are corresponding to R$_2$ as mentioned above and each independently is a hydrocarbon group having not more than 30 carbon atoms or a hydrocarbon group containing an ether bond and having 2 to 30 carbon atoms, R$_5$OH resulting from said carbonate during the course of reaction with said polyol being lower in boiling point from that of said polyol as will be represented by the general formula [III] or [IV], and the carbonate being used in such an amount that the molar ratio of this carbonate to the polyol of the general formula [III] or [IV] is from 3 to 80, is heated in the presence of a basic catalyst, and the mixture is allowed to undergo reaction so as to proceed to a reaction ratio of not less than 95%. In carrying out the above-mentioned reaction, it is desirable that the reactor used therefor is nitrogen substituted, though this is not essential thereto.

Subsequently, the basic catalyst is removed from the reaction product, and the unreacted carbonate is distilled off from the reaction system to obtain the polycarbonate represented by the above-mentioned general formula [I] or [II].

In the process as illustrated above, there is a possibility that there are formed not only the polycarbonates obtained by carbonation of all the hydroxyl groups of the starting polyol but also small amounts of the polycarbonates obtained by carbonation of parts of the hydroxyl groups of this polyol.

The general formula [III] representing the above-mentioned polyol (a) is as follows:

$$Su—O—R_6 \quad \ldots [III]$$

wherein Su is a group represented by the following formula (G), and R6 is a group selected from those represented by the following formulas (H), (I), (J), (K) and (L).

[CH$_2$(OR$_7$)]CH[CH(OR$_7$)]$_3$CH—  (G)
└──── O ────┘

[CH$_2$(OR$_7$)]CH[CH(OR$_7$)]$_2$C[CH$_2$(OR$_7$)]—  (H)
└──── O ────┘

[CH$_2$(OR$_7$)]CH—O—[CH(OR$_7$)]$_3$CH—  (I)
└────────────────┘

CH(OR$_7$)[CH(OR$_7$)]$_3$CHCH$_2$—  (J)
└──────── O ────────┘

In the above-mentioned formulas (G), (H), (I) and (J), R$_7$ is a group represented by the following formula (K) or (L).

—(C$_3$H$_6$O)$_n$H  ...(K)

wherein n is an integer of 1 to 12.

—(C$_3$H$_6$O)$_n$(C$_2$H$_4$O)$_p$H  ...(L)

wherein n and p are each an integer of 1 to 12.

Concrete examples of the polyol represented by the above-mentioned general formula [III] include those represented by the formulas as mentioned below. In these formulas, n is an integer of 1 to 12.
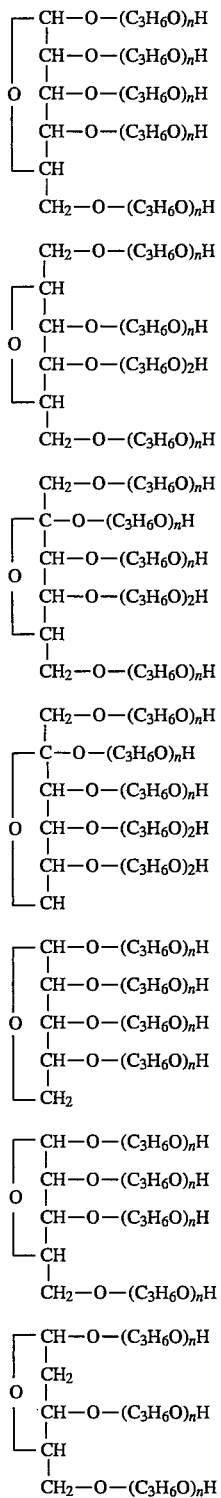
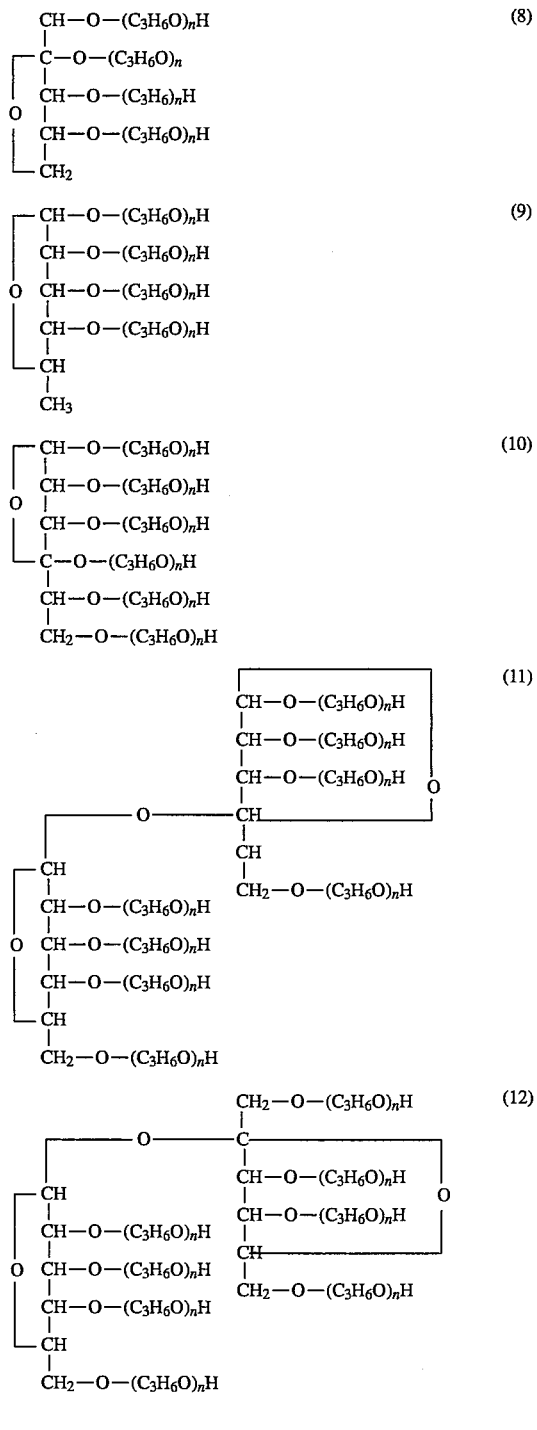

Concrete examples of the polyols represented by the above-mentioned general formula [IV] include those represented by the following formulas. In these formulas mentioned below, n is an integer of 1 to 12.

$$\begin{array}{l} CH_2-O-(C_3H_6O)_nH \\ | \\ CH-O-(C_3H_6O)_nH \\ | \\ CH-O-(C_3H_6O)_nH \\ | \\ CH-O-(C_3H_6O)_nH \\ | \\ CH_2-O-(C_3H_6O)_nH \end{array} \quad (1)$$

$$\begin{array}{l} CH_2-O-(C_3H_6O)_nH \\ | \\ CH_2 \\ | \\ CH-O-(C_3H_6O)_nH \\ | \\ CH-O-(C_3H_6O)_nH \\ | \\ CH_2-O-(C_3H_6O)_nH \end{array} \quad (2)$$

$$\begin{array}{l} CH_2-O-(C_3H_6O)_nH \\ | \\ CO \\ | \\ CH-O-(C_3H_6O)_nH \\ | \\ CH-O-(C_3H_6O)_nH \\ | \\ CH_2-O-(C_3H_6O)_nH \end{array} \quad (3)$$

$$\begin{array}{l} CH_2-O-(C_3H_6O)_nH \\ | \\ CH-O-(C_3H_6O)_nH \\ | \\ CH-O-(C_3H_6O)_nH \\ | \\ CH-O-(C_3H_6O)_nH \\ | \\ CH_3 \end{array} \quad (4)$$

$$\begin{array}{l} CH_2-O-(C_3H_6O)_nH \\ | \\ CH-O-(C_3H_6O)_nH \\ | \\ CH-O-(C_3H_6O)_nH \\ | \\ CH-O-(C_3H_6O)_nH \\ | \\ CH-O-(C_3H_6O)_nH \\ | \\ CH_2-O-(C_3H_6O)_nH \end{array} \quad (5)$$

(6)–(10)

Polyols (6) to (10) are those represented by respectively by the same chemical formulas shown in the foregoing (1) to (5) polyols except that the —$(C_3H_6O)_n$H groups in each formula have been substituted with the —$(C_3H_6O)_n(C_2H_4O)_p$H groups.

The carbonate represented by the above-mentioned general formula [V] which is used preferably in the above-mentioned process for preparing the polycarbonates represented by the general formula [I] or [II] includes concretely dimethyl carbonate, diethyl carbonate, dipropyl carbonate, dibutyl carbonate, dihexyl carbonate, dioctyl carbonate, dicyclohexyl carbonate, di-2-ethylhexyl carbonate and di(2-methylmethoxyethyl)carbonate.

In this process, the carbonation reaction is allowed to proceed while distilling off alcohol resulting from this reaction from the reaction system, hence the thus formed alcohol, that is, alcohol represented by $R_5$OH, must have a boiling point lower than that of the above-mentioned polyol.

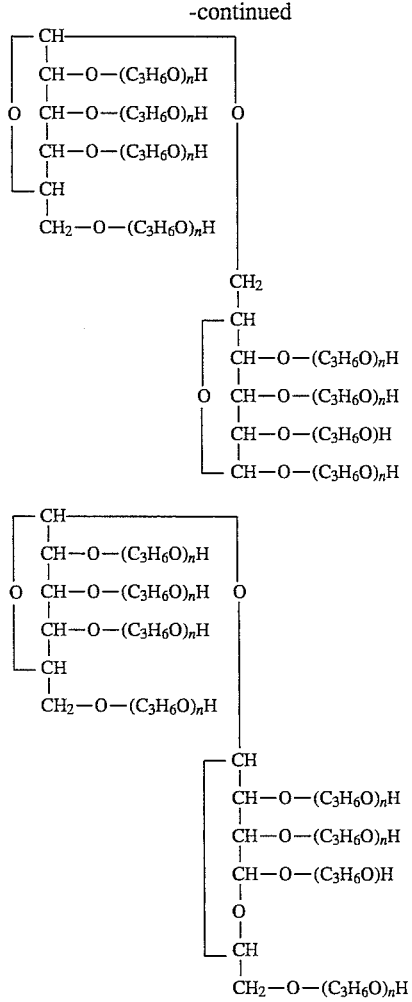

(13)

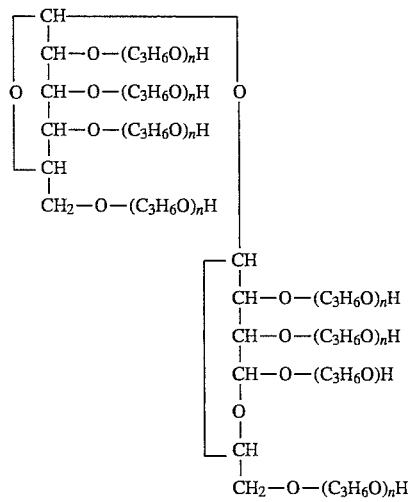

(14)

(15)–(28)

Polyols (15) to (28) are those represented respectively by the same chemical formulas shown in the foregoing (1) to (14) polyols, except that the —$(C_3H_6O)_n$H groups in each formula have been substituted with the —$(C_3H_6O)_n(C_2H_4O)_p$ groups.

The polyols represented by the following general formula [IV] representing the above-mentioned polyol (a) is as follows:

$$(R_7O)CH_2[CH_2(OR_7)]_mCH_2(OR_7) \quad \ldots [IV]$$

wherein $R_7$ is a group represented by the following formula (K) or (L), and m is an integer of 1 to 6.

$$-(C_3H_6O)_nH \quad \ldots (K)$$

wherein n is an integer of 1 to 12.

$$-(C_3H_6O)_n(C_2H_4O)_pH \quad \ldots (L)$$

wherein n and p are each an integer of 1 to 12.

Further, the carbonates exemplified above are used in such an amount that the molar ratio of the carbonate to the polyol of the above-mentioned general formula [III] or [IV] is 3 to 80, preferably 3 to 50. By using the limited amount of the carbonate as defined above, it is possible to inhibit the formation of polycarbonate of high polymerization degree.

In the process mentioned above, the reaction is carried out by heating the above-mentioned polyol and carbonate in the presence of a basic catalyst in the reactor so as to proceed to a reaction ratio of not less than 95% while distilling off the resulting alcohol from the reaction system. After removing the basic catalyst from the reaction product, the unreacted carbonate is distilled off from the reaction system. By the expression ". . . so as to proceed to a reaction ratio of not less than 95%" as used herein is meant that the reaction is continued until the above-mentioned resulting alcohol is formed not less than 0.95 times the molar quantity of the polyol represented by the abovementioned general formula [III] or [IV].

The basic catalyst preferably used in this process includes alkali metal hydroxide such as sodium hydroxide or potassium hydroxide, alkali metal carbonate or hydrogen carbonate such as sodium carbonate or sodium hydrogen carbonate, alkali metal alcoholate such as sodium methoxide, potassium methoxide, lithium methoxide or cesium methoxide, and alkali metal compound such as sodium hydride or sodium amide. Of these basic catalysts, particularly preferred is the alkali metal alcoholate. In addition thereto, there may also be used, for example, alkaline earth metal compound such as magnesium hydroxide or calcium hydroxide, organic amino compound such as trimethylamine, triethylamine, imidazole or tetramethylammonium hydroxide. These catalysts are used in such an amount that the molar ratio (the number of moles of the catalyst/the number of moles of the polyol) is usually $10^{-1}$ to $10^{-7}$, preferably $10^{-2}$ to $10^{-5}$.

In the process of the invention mentioned above, the reaction is carried out at a temperature of usually 50° to 300° C. preferably 60° to 200° C. and the reaction time is usually 0.5 to 200 hours, preferably 1 to 100 hours.

Removal of the catalyst after the completion of the reaction is carried out by washing with water or by neutralizing with acid. The acid used herein includes solid acids such as sulfonic acid type ion exchange resins; inorganic acids such as carbonic acid, ammonium chloride, hydrochloric acid, sulfuric acid and phosphoric acid; and organic acids such as acetic acid and phenol. In carrying out the water washing as mentioned above, such a salt as ammonium carbonate may be added to the water.

According to the process of the invention carried out in the manner now described, polymerization of the polycarbonate can be inhibited, said polymerization being caused by distilling off the unreacted carbonate in the presence of the basic catalyst, by removing first the basic catalyst and then distilling off the unreacted carbonate under reduced pressure, and hence the desired polycarbonate can be obtained in high yield.

The thus obtained polycarbonate may be freed from a trace amount of impurities, if necessary, by treating it with adsorbents such as activated clay and activated carbon or by washing it with water. In particular, a trace amount of ionic or polar compounds can be removed by such treatment as mentioned above from the polycarbonate obtained above, the polycarbonate thus treated can be stored stably.

When dimethyl carbonate is used as the starting carbonate in the reaction of the above-mentioned process of the invention, an azeotrope former such as cyclohexane, benzene or hexane may be added to the reaction system before initiation of the reaction, whereby methanol produced may be removed from the reaction system as an azeotropic mixture with the azeotrope former instead of removing methanol as an azeotropic mixture with dimethyl carbonate from the reaction system. The azeotrope former is usually used in an amount of 5 to 100% by weight based on 100% by weight of dimethyl carbonate.

According to the procedure mentioned above, methanol is removed during the course of reaction as an azeotropic mixture with the above-mentioned azeotrope former from the reaction system, and the unreacted dimethyl carbonate is recovered from the reaction mixture after completion of the reaction, and hence the recovery thereof can be increased.

There is another procedure wherein methanol is recovered as an azeotropic mixture with dimethyl carbonate as described above, the above-mentioned azeotrope former is then added to the azeotropic mixture to remove methanol as an azeotropic mixture with said azeotrope formed from dimethyl carbonate, and dimethyl carbonate can be thus recovered.

According to the process of the invention as illustrated above, the desired polycarbonates can be obtained in high yields, because the basic catalyst used is removed from the reaction product after completion of the reaction of the polyol with carbonate, and the unreacted carbonate is then removed from the reaction system. Furthermore, the polycarbonates represented by the general formula [I] or [II] may also be prepared by the process as will be mentioned hereinafter.

First, a mixture comprising (a) a polyol represented by the aforementioned general formula [III] or [IV], (b) a monoalcohol represented by the following general formula [VI]:

$R_8OH$ ... [VI]

wherein $R_8$ is the same as $R_2$ defined in the aforementioned general formula (E), and (c) a carbonate represented by the following general formula [VII]:

$R_9OCOOR_9$ ... [VII]

wherein $R_9$ are each independently an alkyl group having 1 to 2 carbon atoms, $R_9OH$ resulting from said carbonate during the course of reaction with said polyol and monoalcohol being lower in boiling point than those of said polyol and monoalcohol, and said carbonate being used in such an amount that the molar ratio of the carbonate to the polyol of the general formula [III] or [IV] is 3 to 80, is heated in the presence of a basic catalyst, and the mixture is allowed to undergo reaction so as to proceed to a reaction ratio of not less than 95%, while distilling off the resulting alcohol ($R_9OH$) from the reaction system. In carrying out this reaction, it is desirable that the reactor used therefore is nitrogen substituted, though this is not essential thereto.

Subsequently, the basic catalyst is removed from the reaction product, and the unreacted carbonate is distilled off from the reaction system to obtain the polycarbonate represented by the above-mentioned general formula [I] or [II].

Even in this process as illustrated above, there is still a possibility that there are formed not only the polycarbonates obtained by complete carbonation of the hydroxyl groups of the starting polyol but also small amounts of the polycarbonates obtained by partial carbonation of the hydroxyl groups of this polyol.

In this process, the carbonation reaction is allowed to proceed while distilling off alcohol resulting from this reaction from the reaction system, hence the thus formed alcohol, that is, alcohol represented by $R_9OH$, must have a boiling point lower than those of the above-mentioned polyol and monoalcohol.

Further, the carbonates exemplified above are used in such an amount that the molar ratio of the carbonate to the polyol of the above-mentioned general formula [III] or [IV] is 3 to 80, preferably 3 to 50. By using the limited amount of the carbonate as defined above, it is possible to inhibit the formation of polycarbonates of high polymerization degree.

In the process mentioned above, the reaction is carried out by heating the above-mentioned polyol, monoalcohol and carbonate charged in the reactor in the presence of a basic catalyst so as to proceed to a reaction ratio of not less than 95%, while distilling off the resulting alcohol from the reaction system. After removing the basic catalyst from the reaction product, the unreacted carbonate is distilled off from the reaction system. By the expression ". . . so as to proceed to a reaction ratio of not less than 95%" as used herein is meant that the reaction is continued until the above-mentioned resulting alcohol is formed not less than 0.95 times the molar quantity of the polyol represented by the above-mentioned general formula [III] or [IV].

With respect to the basic catalyst, reaction temperature, reaction time, removal of the catalyst after completion of the reaction, removal of impurities from the end product and recovery of the unreacted dimethyl carbonate, this process of the invention as mentioned above is carried out in the same manner as in the process of the invention as mentioned previously.

In the process of the invention as first mentioned, the carbonates other than dimethyl carbonate and diethyl carbonate represented by the general formula [V] must be synthesized when they are used, because they are difficult to obtain commercially. On the other hand, in the process of the invention just described above, the desired polycarbonates can be prepared by using easily available carbonates represented by the general formula [VII] (dimethyl carbonate, diethyl carbonate and ethylmethyl carbonate), hence this process is more economical than the process as first mentioned.

Furthermore, the desired polycarbonates can be obtained in high yields in the manner similar to the case of the process as first mentioned.

The polycarbonates of the present invention are excellent in lubricating properties as well as in detergency and, at the same time, they are also excellent, though they are highly viscous, in compatibility with an ozone layer-undestructive hydrogenated fluorocarbon such as Freon R-134a, with a hydrogenated chlorofluorocarbon having a small ozone destructive power such as Freon R-22 and further with mixtures thereof.

Accordingly, the polycarbonates of the invention can be utilized as lubricant oils for refrigerators wherein highly viscous lubricant oils are used.

The lubricant oils of the invention such as lubricant oils for refrigerators contain at least one of the polycarbonates of the invention as mentioned above, that is, the polycarbonate represented by the general formula [I] or [II]. Accordingly, the lubricant oils of the invention such as lubricant oils for refrigerators may contain both the polycarbonate of the general formula [I] and the polycarbonate of the general formula [II]. In addition to the polycarbonates of the general formulas [I] and [II], the lubricant oils of the invention such as lubricant oils for refrigerators may contain further other polycarbonates, for example, those derived from lower aliphatic hydrocarbon polyether glycols.

The lubricant oils of the invention such as lubricant oils for refrigerators may contain other components in addition to the polycarbonates as mentioned above.

In addition to the polycarbonates of the invention, the lubricant oils of the invention may be loaded with other usable components such as glycol ethers, for example, polyether glycol of a random copolymer of ethylene oxide and propylene oxide, carbonates derived from this polyether glycol, for example, dicarbonates and monocarbonates, and mineral oils, for example, neutral oil or bright stock, and further with e-olefin oligomer such as liquid polybutene, and liquid decene oligomer, carboxylic acid ester such as diisooctyl adipate, diisooctyl sebacate and dilauryl sebacate, or vegetable oils.

Particularly, the lubricating oil of the invention may contain, in addition to at least one of the polycarbonates selected from the group consisting of the polycarbonates (I) and (II), a monocarbonate represented by the following general formula (XXX):

$R_i OCOOR_{ii}$ ...(XXX)

wherein each of $R_i$ and $R_{ii}$ is independently a hydrocarbon group having 1–36 carbon atoms, or a glycol ether group represented by the following general formula (XXXI):

$R_{iii}(OR_{iv})_l$— ...(XXXI)

wherein $R_{iii}$ is a hydrocarbon group having 1–6 carbon atoms, $R_{iv}$ is ethylene group or propylene group and l is an integer of 1–100.

Concrete examples of the hydrocarbon groups represented by $R_i$ and $R_{ii}$ include methyl, ethyl, propyl, isopropyl, isobutyl, s-butyl, t-butyl, pentyl, isopentyl, neopentyl, n-hexyl, isohexyl, n-nonyl, isononyl, isododecyl, stearyl, oleyl and cyclohexyl groups.

Further, concrete examples of the glycol ether group represented by $R_i$ and $R_{ii}$ are those in which as the above-mentioned $R_{iii}$ in the general formula (XXXI) include methyl, ethyl, propyl, isopropyl, isobutyl, s-butyl, t-butyl, pentyl, isopentyl, neopentyl, cyclohexyl and phenyl groups.

$R_{iv}$ includes ethylene and propylene group.

The monocarbonate, which is represented by the formula (XXX) wherein $R_i$ or $R_{ii}$ is the glycol ether group represented by the formula (XXXI), are especially excellent in the lubricating properties against aluminum and can effectively prevent aluminum parts of a machine from abrasion. Accordingly, the lubricating oil of the invention containing the monocarbonate is prefereably used as a lubricant agent used for the machine having the aluminum parts.

The monocarbonate represented by the above formula (XXX) includes, for example, the following monocarbonates.

(1) $CH_3O(C_3H_6O)_n(C_2H_4O)_{m-1}C_2H_4OCOO(C_3H_6O)_n—(C_2H_4O)_mCH_3$ (2) $C_2H_5O(C_3H_6O)_n(C_2H_4O)_{m-1}C_2H_4OCOO(C_3H_6O)_n—(C_2H_4O)_mC_2H_5$ (3) $C_3H_7O(C_3H_6O)_n(C_2H_4O)_{m-1}C_2H_4OCOO(C_3H_6O)_n—(C_2H_4O)_mC_4H_9$.

(4) $C_4H_9O(C_3H_6O)_n(C_2H_4O)_{m-1}C_2H_4OCOO(C_3H_6O)_n—(C_2H_4O)_mC_4H_9$ (5) $CH_3OCOO(C_3H_6O)_n(C_2H_4O)_mCH_3$ (6) $C_3H_7OCOO(C_3H_6O)_n(C_2H_4O)_mCH_3$ (7) $CH_3OCOO(C_3H_6O)_n(C_2H_4O)_mC_3H_7$ (8) $C_2H_5OCOO(C_3H_6O)_n(C_2H_4O)_mC_2H_5$

In the above formula (1)–(8), each of n and m represents an integer of 0–100, provided that n+m is in the range of 1–100.

Further, in the case of the lubricating oils of the invention used as a lubricating oil for refrigerators wherein HFC, for example, Freon R-134a is used as an ozone layer-nondestructive refrigerant, the above-mentioned other usable components are limited to carbonates, glycol ethers or carboxylic acid esters from the standpoint of compatibility. In that case, however, the amount of these usable components loaded to the lubricating oil must be limited to less than 60% by weight based on 100% by weight of the total amount of the lubricating oil, otherwise the lubricating oil thus loaded will deteriorate in heat resistance, compatibility with Freon R-134a and hygroscopicity.

Further, the lubricant oils for refrigerators of the invention may also be loaded with an epoxy compound as a chlorine complementary agent used against inclusion into the lubricant oil of a phenolic stabilizer, defoaming agent or chlorine refrigerant.

Furthermore, in the present invention, it is possible to contain in the lubricant oils of the invention for use in refrigerators such known additives for lubricant oil, for example, detergent-dispersants, antioxidants, anti-load agents, oiliness improvers and pour point depressants as disclosed in "Additives for Petroleum Products" compiled by T. Sakurai, Saiwai Shobo, 1974 in such an amount that the objects of the present invention can be accomplished without hindrance.

Still further, the lubricant oils for refrigerators of the invention may also contain an ozone layer-nondestructive Freon .(HFC) such as Freon R-134a, Freon (HCFC) having a small ozone-destructive force such as Freon R-22 and mixtures thereof.

The third novel polycarbonates of the invention and the uses thereof are illustrated hereinafter.

The third novel polycarbonates of the invention are represented by the following general formula [VIII].

$$(CH_3)_xC(CH_2OCOOR_{10})_y \qquad \ldots [VIII]$$

wherein $R_{10}$ each independently represents a hydrocarbon group having not more than 30 carbon atoms or a hydrocarbon group containing an ether bond and having 2 to 30 carbon atoms, x is an integer of 0 to 2, and y is an integer of 2 to 4.

The hydrocarbon groups represented by $R_{10}$ of the above general formula [VIII] include aliphatic hydrocarbons, alicyclic hydrocarbons, aromatic hydrocarbons, aromatic aliphatic hydrocarbons and glycol ethers represented by the following general formula $$-(R_{11}-O)_qR_{12}$$

wherein $R_{11}$ is an alkylene group having 2 to 3 carbon atoms, $R_{12}$ is a hydrocarbon group having not more than 28 carbon atoms, and q is an integer of 1 to 20.

The polycarbonates represented by the above-mentioned general formula [VIII] may include, for example, those having the following chemical formulas.

(1) $(CH_3)_2C[CH_2OCOOCH_2CH(C_2H_5)C_4H_9]_2$
(2) $(CH_3)_2C[CH_2OCOOCH(CH_3) \ CH_2CH \ (CH_3) \ 2]_2$
(3) $(CH_3)_2C[CH_2OCOOCH(CH_3)_2]_2$
(4) $(CH_3)_2C[CH_2OCOOCH(CH_3)C_3H_7]_2$
(5) $(CH_3)_2C[CH_2OCOOCH(CH_3)C_4H_9]_2$
(6) $(CH_3)_2C[CH_2OCOOCH_2CH(CH_3)C_4H_9]_2$
(7) $(CH_3)_2C[CH_2OCOOCH(CH_3)CH_2CH(CH_3)C_2H_5]_2$
(8) $C[CH_2OCOOC_4H_9]_4$
(9) $C[CH_2OCOOCH(CH_3)_2]_4$
(10) $C[CH_2OCOOCH(CH_3)C_2H_5]_4$
(11) $C[CH_2OCOOCH(CH_3)C_3H_7]_4$
(12) $C[CH_2OCOOCH_2CH(CH_3)C_4H_9]_4$
(13) $C[CH_2OCOOC_9H_{19}]_4$
(14) $C[CH_2OCOOC_{10}H_{21}]_4$
(15) $C[CH_2OCOOC_3H_6OC_3H_7]_4$
(16) $C[CH_2OCOOC_2H_4OC_3H_7]_4$
(17) $(CH_3)C[CH_2OCOOCH(CH_3)_2]_3$
(18) $(CH_3)C[CH_2OCOOCH(CH_3)C_2H_5]_3$
(19) $(CH_3)C[CH_2OCOOCH(CH_3)C_3H_7]_3$
(20) $(CH_3)C[CH_2OCOOCH_2CH(CH_3)C_4H_9]_3$
(21) $(CH_3)C[CH_2OCOOC_9H_{19}]_3$
(22) $(CH_3)C[CH_2OCOOC_{10}H_{21}]_3$
(23) $(CH_3)C[CH_2OCOOC_3H_6OC_3H_7]_3$
(24) $(CH_3)C[CH_2OCOOC_2H_4OC_3H_7]_3$

Preferred polycarbonates represented by the abovementioned general formula [VIII] are, for example, those represented by the following formulas.

(1) $(CH_3)_2C(CH_2OCOOR_{10})_2$, and
(2) $C(CH_2OCOOR_{10})_4$

In the above formulas (1) and (2), $R_{10}$ represents the same groups as represented by $R_{10}$ in the above-mentioned general formula [VIII].

The polycarbonates represented by the general formula [VIII] may be prepared, for example, by the process as will be disclosed hereinafter.

First, a mixture comprising (a) a polyol represented by the following general formula [IX]:

$$(CH_3)_xC(CH_2OH)_y \qquad \ldots [IX]$$

wherein x and y are each as defined by x and y, respectively in the above-mentioned general formula [VIII], and (b) a carbonate represented by the following general formula [X]:

$$R_{10}OCOOR_{10} \qquad \ldots [X]$$

wherein R10 is the same as $R_{10}$ in the above-mentioned formula [VIII], $R_{10}OH$ resulting from said carbonate during the course of reaction with said polyol being lower in boiling point than that of said polyol, and said carbonate being used in such an amount that the $m_1/ym_2$ ratio (wherein ml is the number of mols of the carbonate, $m_2$ is the number of mols of the polyol, and y is the number of hydroxyl groups of the polyol) is 2 to 200, is heated in the presence of a basic catalyst, and the mixture is allowed to undergo reaction so as to proceed to a reaction ratio of not less than 95%, while distilling off the resulting alcohol ($R_{10}OH$) from the reaction system. In carrying out this reaction, it is desirable that the reactor used therefor is nitrogen substituted, though this is not essential thereto.

Subsequently, the basic catalyst is removed from the reaction product, and the unreacted carbonate is distilled off from the reaction system to obtain an aliphatic polycarbonate represented by the above-mentioned general formula [VIII].

Concrete examples of the carbonates represented by the above-mentioned general formula [X] include dimethyl carbonate, diethyl carbonate, dipropyl carbonate, dibutyl carbonate, di-[1,3-dimethylbutyl]carbonate, dihexyl carbonate, dioctyl carbonate, di-[2-ethylhexyl]carbonate and dicyclohexyl carbonate.

In the process as illustrated above, the carbonation reaction is allowed to proceed while distilling off the alcohol resulting from this reaction out of the reaction system, hence this alcohol, that is, $R_{10}OH$, must be lower in boiling point than the above-mentioned polyol.

The carbonate is used in this process in such an amount that the $m_1/ym_2$ ratio (wherein $m_1$ is the number of mols of the carbonate, $m_2$ is the number of mols of the polyol, and y is the number of hydroxyl groups of the polyol) is 2 to 200, preferably 3 to 80 and especially 3 to 50. By using the limited amount of the carbonate as defined above, it is possible to inhibit the formation of polycarbonates of high polymerization degree.

In the process as illustrated above, the reaction is carried out by charging a reactor with the above-mentioned polyol and carbonate, heating the charge in the presence of a basic catalyst, distilling off the resulting alcohol out of the reaction system, allowing the reaction to proceed to a reaction ratio of not less than 95%, removing the basic catalyst from the reaction product, and distilling off the unreacted carbonate out of the reaction system. By the reaction ratio of not less than 95% as used herein is meant that the reaction is allowed to proceed until the resulting alcohol mentioned above is formed at least 0.95 times the molar quantity of the above-mentioned $ym_2$.

With respect to the basic catalyst, reaction temperature, reaction time, removal of the catalyst after completion of the reaction, removal of impurities from the end product and recovery of the unreacted dimethyl carbonate, this process as mentioned above is carried out in the same manner as in the process for preparing the polycarbonates represented by the above-mentioned general formulas [I] and [II].

The polycarbonates represented by the general formula [VIII] may also be prepared by the following process.

First, a mixture comprising (a) a polyol represented by the following general formula [IX]:

$$(CH_3)_xC(CH_2OH)_y \quad \ldots [IX]$$

wherein x is an integer of 0 to 2 and y is an integer of 2 to 4, (b) a monoalcohol represented by the following general formula [XI]:

$$R_{10}OH \quad \ldots [XI]$$

wherein $R_{10}$ is the same as $R_{10}$ defined in the above-mentioned general formula [VIII], and (c) a carbonate represented by the following general formula [XII]:

$$R_{13}OCOOR_{13} \quad \ldots [XII]$$

wherein $R_{13}$ are each independently an alkyl group having 1 to 2 carbon atoms, $R_{13}OH$ resulting from said carbonate during the course of reaction with said polyol being lower in boiling point than said polyol, and said carbonate being used in such an amount that the $m_1/ym_2$ ratio (wherein $m_1$ is the number of mols of the carbonate, $m_2$ is the number of mols of the polyol, and y is the number of hydroxyl groups of the polyol) is 2 to 200, is heated in the presence of a basic catalyst, and the mixture is allowed to undergo reaction so as to proceed to a reaction ratio of not less than 95%, while distilling off the resulting alcohol ($R_{13}OH$) from the reaction system. In carrying out this reaction mentioned above, it is desirable that the reactor is nitrogen substituted, though this is not essential thereto.

Subsequently, the basic catalyst is removed from the reaction product, and the unreacted carbonate and carbonate which has not participated in the final stage reaction ($R_{14}OCO_2R_{14}$ wherein $R_{14}$ are each independently the same as $R_{10}$ or $R_{13}$ as defined previously) are distilled off out of the reaction system to obtain the polycarbonates represented by the general formula [VIII].

In this process as illustrated above, the carbonation reaction is allowed to proceed while distilling off the alcohol ($R_{13}OH$) resulting from this reaction out of the reaction system, hence the alcohol represented by $R_{13}OH$ must be lower in boiling point than the above-mentioned polyol.

The above-mentioned carbonate is used in such an amount that the $m_1/ym_2$ ratio (wherein ml is the number of mols of the carbonate, $m_2$ is the number of mols of the polyol, and y is the number of hydroxyl groups of the polyol) is 2 to 200, preferably 3 to 80 and especially 3 to 50. By using the limited amount of the starting carbonate as defined above, it is possible to inhibit the formation of polycarbonates of high polymerization degree.

In the process mentioned above, the reaction is carried out by heating the above-mentioned polyol, monoalcohol and carbonate charged in the reactor in the presence of a basic catalyst so as to proceed to a reaction ratio of not less than 95%, while distilling off the resulting alcohol out of the reaction system. After removing the basic catalyst from the reaction product, the unreacted carbonate is distilled off out of the reaction system. The reaction ratio of not less than 95% signifies that the reaction is allowed to proceed until the above-mentioned alcohol is formed at least 0.95 times the molar quantity of the above-mentioned $ym_2$.

With respect to the above-mentioned basic catalyst, reaction temperature, reaction time, removal of the catalyst after completion of the reaction, removal of impurities and recovery of the unreacted dimethyl carbonate, the above-mentioned process is carried out in the same manner as in the process for preparing the polycarbonates represented by the general formulas [I] and [II] mentioned previously.

The polycarbonates represented by the above-mentioned general formula [VII] are excellent in lubricating properties and have a volume resistivity on the order of $10^{13}$ to $10^{14}$ $\Omega$.cm, thus they are high in electrical insulation properties in comparison with conventional polycarbonates. Accordingly, the polycarbonates of the general formula [VIII] can be used as lubricant oils requiring electrical insulation properties, in particular, and electrical insulating oils, concretely as lubricant oils and electrical insulating oils for electric refrigerators.

The above-mentioned polycarbonates are excellent in compatibility with an ozone layer-nondestructive Freon such as Freon R-134a, hence they are suitable for use in lubricant oils for refrigerators wherein an ozone layer-nondestructive Freon is used as a refrigerant.

The lubricant oils, such as those for refrigerators, containing the polycarbonates represented by the above-mentioned general formula [VIII] may contain other components than said polycarbonates in the same manner as in the case of the lubricant oils for refrigerators containing the polycarbonates represented by the above-mentioned general formulas [I] and [II].

The fourth novel polycarbonates of the invention and uses thereof are illustrated hereinafter.

The fourth novel polycarbonates of the invention are represented by the following general formula [XIII].

$$R_{15}OCOOR_{16}OCOOR_{17} \quad \ldots [XIII]$$

wherein $R_{15}$ and $R_{17}$ each are independently a hydrocarbon group having not more than 30 carbon atoms or a hydrocarbon group containing an ether bond and having 2 to 30 carbon atoms, and $R_{16}$ is a straight chain or branched hydrocarbon group having the total carbon atoms of 5 to 8, the main chain of which has 4 to 8 carbon atoms.

The hydrocarbon group represented by $R_{16}$ includes amylene, methylamylene, ethylamylene, hexylene, methylhexylene, ethylhexylene, etc.

The hydrocarbon groups represented by the above-mentioned $R_{15}$ and $R_{17}$, respectively, include aliphatic hydrocarbons, alicyclic hydrocarbons, aromatic hydrocarbons, aromatic aliphatic hydrocarbons and a glycol ether group represented by the following general formula $$-(R_{18}-O)_q-19$$

wherein $R_{18}$ is an alkylene group having 2 to 3 carbon atoms, $R_{19}$ is a hydrocarbon group having not more than 28 carbon atoms, and q is an integer of 1 to 20.

Concrete examples of the groups represented by the above-mentioned $R_{15}$ and $R_{17}$, respectively, include the same groups as those of the aliphatic hydrocarbons, alicyclic hydrocarbons, aromatic hydrocarbons and glycol ethers represented by the above-mentioned $R_2$.

The polycarbonates represented by the above-mentioned general formula [XIII] include concretely those having the following chemical formulas, respectively.

(1) $CH_3C_2H_4CH(CH_3)C_2H_4-OCOO-C_2H_4CH(CH_3)C_2H_4-OCOO-C_2H_4CH(CH_3)C_2H_4CH_3$
(2) $CH_3CH(CH_3)C_4H_8-OCOO-C_2H_4CH(CH_3)C_2H_4-OCOO-C_4H_8CH(CH_3)CH_3$
(3) $C_4H_9CH(C_2H_5)CH_2-OCOO-C_2H_4CH(CH_3)C_2H_4-OCOO-CH_2CH(C_2H_5)C_4H_9$
(4) $C_3H_7C(CH_3)_2CH_2-OCOO-C_2H_4CH(CH_3)C_2H_4-OCOO-CH_2C(CH_3)_2C_3H_7$
(5) $C_4H_9(CH_3)CHCH_2-OCOO-C_2H_4CH(CH_3)C_2H_4-OCOO-CH_2CH(CH_3)C_4H_9$
(6) $C_4H_9(CH_3)CHC_2H_4-OCOO-C_2H_4CH(CH_3)C_2H_4-OCOO-C_2H_4CH(CH_3)C_4H_9$
(7) $C_3H_7OC_2H_4-OCOO-C_2H_4CH(CH_3)C_2H_4-OCOO-C_2H_4OC_3H_7$
(8) $C_4H_9OC_2H_4-OCOO-C_2H_4CH(CH_3)C_2H_4-OCOO-C_2H_4OC_4H_9$
(9) $C_2H_5OC_3H_6-OCOO-C_2H_4CH(CH_3)C_2H_4-OCOO-C_3H_6OC_2H_5$
(10) $(C_2H_5OCH_2)_2CH-C_2H_4CH(CH_3)C_2H_4-OCOO-CH(CH_2OC_2H_5)_2$
(11) $CH_3C_2H_4CH(CH_3)C_2H_4-OCOO-C_2H_4CH(CH_3)C_3H_6-OCOO-C_2H_4CH(CH_3)C_2H_4CH_3$
(12) $CH_3CH(CH_3)C_4H_8-OCOO-C_3H_6CH(CH_3)C_3H_6-OCOO-C_4H_8CH(CH_3)CH_3$
(13) $C_4H_9CH(C_2H_5)CH_2-OCOO-C_5H_{10}-OCOO-CH_2CH(C_2H_5)C_4H_9$
(14) $C_3H_7CH(CH_3)_2CH_2-OCOO-C_6H_{12}-OCOO-CH_2C(CH_3)_2C_3H_7$
(15) $C_4H_9(CH_3)CHCH_2-OCOO-C_4H_8CH(CH_3)C_2H_4-OCOO-CH_2CH(CH_3)C_4$

Preferred polycarbonates represented by the above-mentioned general formula [XIII] are, for example, those having the above-mentioned chemical formulas (1) to (10), respectively, that is, those represented by the following general formula.

$$R_{15}OCOO-C_2H_4CH(CH_3)C_2H_4-OCOOR_{17} \quad (1)$$

wherein $R_{15}$ and $R_{17}$ are as defined in the above-mentioned general formula [XIII].

The polycarbonates represented by the above-mentioned general formula [XIII] may be prepared, for example, by the following process.

First, a mixture comprising
(a) a diol represented by the following general formula [XIV]:

$$R_{16}(OH)_2 \quad \ldots [XIV]$$

wherein $R_{16}$ is as defined in the above-mentioned general formula [XIII], and
(b) a carbonate represented by the following general formula [XV]:

$$R_{15}OCOOR_{15} \text{ or } R_{17}OCOOR_{17} \quad \ldots [XV]$$

wherein $R_{15}$ and $R_{17}$ are as defined in the above-mentioned general formula [XIII], the resulting $R_{15}OH$ or $R_{17}OH$ from said carbonate during the course of reaction with said diol being lower in boiling point than said diol, and said carbonate being used in such an amount that the $m_3/2m_4$ ratio (wherein $m_3$ is the number of mols of the carbonate, and $m_4$ is the number of mols of the diol) is 2 to 200, is heated in the presence of a basic catalyst, and the mixture is allowed to undergo reaction to proceed to a reaction ratio of not less than 95%, while distilling off the resulting alcohol ($R_{15}OH$ or $R_{17}OH$) out of the reaction system. In carrying out the above-mentioned reaction, it is desirable that the reactor used therefor is nitrogen purged, though this is not essential thereto.

Subsequently, after removal of the above-mentioned basic catalyst from the reaction product, the unreacted carbonate is distilled off out of the reaction system to obtain the polycarbonates represented by the above-mentioned general formula [XIII].

The carbonate represented by the above-mentioned general formula [XV] which is used as the starting carbonate includes concretely dimethyl carbonate, diethyl carbonate, dipropyl carbonate, dibutyl carbonate, di-[1,3dimethylbutyl] carbonate, dihexyl carbonate, dioctyl carbonate, di-[2-ethylhexyl]carbonate and dicyclohexyl carbonate.

According to the process as illustrated above, the carbonation reaction is allowed to proceed while distilling off alcohol resulting from said reaction out of the reaction system, hence the resulting alcohol, i.e. $R_{15}OH$ or $R_{17}OH$, must be lower in boiling point than the above-mentioned diol.

The starting carbonate is used in such an amount that the $m_3/2m_4$ ratio (wherein $m_3$ is the number of mols of the carbonate, and $m_4$ is the number of mols of the diol) is 2 to 200, preferably 3 to 80 and especially 3 to 50. By using the limited amount of the starting carbonate as defined above, it is possible to inhibit the formation of polycarbonates of high polymerization degree.

In the process mentioned above, the reaction is carried out by heating the above-mentioned diol and carbonate charged in the reactor in the presence of a basic catalyst, and allowing the charge to undergo reaction so as to proceed to a reaction ratio of not less than 95%, while distilling off the resulting alcohol out of the reaction system. After removing the basic catalyst from the reaction product, the unreacted carbonate is distilled off out of the reaction system. The reaction ratio of not less than 95% signifies that the reaction is allowed to proceed until the above-mentioned alcohol is formed at least 0.95 times the molar quantity of the above-mentioned $2m_4$. With respect to the above-mentioned basic catalyst, reaction temperature, reaction time, removal of the catalyst after completion of the reaction, removal of impurities and recovery of the unreacted dimethyl carbonate, the above-mentioned process is carried in the same manner as in the process for preparing the polycarbonates represented by the general formulas [I] and [II] mentioned previously.

The polycarbonates represented by the general formula XIII] may also be prepared by the following process.

First, a mixture comprising
(a) a diol represented by the following general formula [XIV]:

(b) a monoalcohol represented by the following general formula [XVI]:R$_{16}$(OH)$_2$ wherein R$_{16}$ is as defined in the above-mentioned general formula [XIII], $$R_{15}OH \text{ or } R_{17}OH \qquad \ldots [XVI]$$

wherein R$_{15}$ and R$_{17}$ are the same as R$_{15}$ and R$_{17}$ in the above-mentioned general formula [XIII], and (c) a carbonate represented by the following general formula [XVII]:

$$R_{20}OCOOR_{20} \qquad \ldots [XVII]$$

wherein R$_{20}$ are each independently an alkyl group having 1 to carbon atoms, the resulting R$_{20}$OH from said carbonate during the course of reaction with said diol being lower in boiling point than said diol, and said carbonate being used in such an amount that the m$_3$/2m$_4$ ratio (wherein m$_3$ is the number of tools of the carbonate, and m$_4$ is the number of mols of the diol) is 2 to 200, is heated in the presence of a basic catalyst, and the mixture is allowed to undergo reaction to proceed to a reaction ratio of not less than 95% while distilling off the resulting alcohol (R$_{20}$OH) out of the reaction system. In carrying out the above-mentioned reaction, it is desirable 0 that t,he reactor used therefor is nitrogen purged, though this is not essential thereto.

Subsequently, after removal of the above-mentioned basic catalyst, the unreacted carbonate and the carbonate which has not participated in the final stage reaction (R$_{21}$OCO$_2$R$_{21}$ wherein R$_{21}$ are each independently R$_{15}$, R$_{17}$ or R$_{19}$ as mentioned previously) are distilled off out of the reaction system to obtain the polycarbonates represented by the above-mentioned general formula [XIII].

In the process mentioned above, the carbonation reaction is allowed to proceed while distilling off alcohol resulting therefrom out of the reaction system, hence the resulting alcohol, i.e. the alcohol represented by R$_{20}$OH must be lower in boiling point than the above-mentioned diol and monoalcohol. The starting carbonate is used in such an amount that the m$_3$/2m$_4$ ratio (wherein m$_3$ is the number of mols of the carbonate, and m4 is the number of mols of the diol) is 2 to 200, preferably 3 to 50. By using the limited amount of the starting carbonate as defined above, it is possible to inhibit the formation of polycarbonates of high polymerization degree.

In the above mentioned process, the reaction is carried out by heating the above-mentioned diol and carbonate charged in the reactor in the presence of a basic catalyst, and allowing the charge to undergo reaction so as to proceed to a reaction ratio of not less than 95% while distilling off the resulting alcohol out of the reaction system. After removal of the basic catalyst, the unreacted carbonate is then distilled off out of the reaction system. The term "the reaction ratio of not less than 95%" as used herein signifies that the reaction is allowed to proceed until the above-mentioned alcohol is formed at least 0.95 times the molar quantity of the above-mentioned 2m$_4$.

With respect to the above-mentioned basic catalyst, reaction temperature, reaction time, removal of the catalyst after completion of the reaction, removal of impurities from the reaction product and recovery of the unreacted carbonate, the above-mentioned process is carried in the same manner as in the process for preparing the polycarbonates represented by the general formulas [I] and [II] as mentioned previously.

The polycarbonates represented by the above-mentioned general formula [XIII] are excellent in lubricating properties and have a volume resistivity on the order of $10^{19}$ to $10^{15}$ Ω.cm, thus they are excellent in electrical insulation properties in comparison with the conventional polycarbonates. Accordingly, the polycarbonates of the general formula [XIII] can be used as lubricant oils and electrical insulating oils requiring particularly electrical insulation properties, and concretely they are suitable for use in lubricant oils and electrical insulating oils for electric refrigerators, in particular.

The above-mentioned polycarbonates of the general formula [XIII] are excellent in compatibility with an ozone layer-nondestructive Freon (HFC) such as Freon R-134a and R-152a, a Freon (HCFC) having a small ozone destructive ability such as Freon R-22, R-123 and R-124, and with mixtures thereof, hence these polycarbonates are suitable for use as lubricant oils for refrigerators using refrigerants such Freons as mentioned above and mixtures thereof.

The lubricant oils, such as those for refrigerators or the like which contain the polycarbonates of the above-mentioned general formula [XIII] may contain additionally other components in the same manner as in the case of lubricant oils such as those for refrigerators containing the polycarbonates represented by the aforementioned general formulas [I], [II], and [VIII].

Further, when the polycarbonates represented by the general formulas [I], [II], [VIII] and [XIII] of the present invention, from which the aforementioned lubricant oils are prepared, are used as rolling lubricant oils, metal working oils and lubricant oils for fibers, it is also possible to use these carbonates in the form of an emulsion in water.

This process for preparing the polycarbonates of the present invention is illustrated hereinafter in detail.

The process of the invention for preparing the polycarbonates is a process for preparing polycarbonates represented by the following general formula [XVIII]:

$$R_{22}(OCOO\text{---}R_{23})_l \qquad \ldots [XVIII]$$

wherein R$_{22}$ is an aliphatic hydrocarbon group having 4 to 300 carbon atoms, an aliphatic hydrocarbon group containing an ether bond and having 4 to 300 carbon atoms or a cyclic hydrocarbon group containing an ether bond and having 6 to 300 carbon atoms, R$_{23}$ is a hydrocarbon group having not more than 30 carbon atoms or a hydrocarbon group containing an ether bond and having 2 to 30 carbon atoms, and 1 is an integer of 2 to 8.

The polycarbonates represented by the above-mentioned general formula [XVIII] include, for example, such polycarbonates as represented by the aforementioned general formulas [I], [II], [VIII] and [XIII].

In the present invention, there are used specific polyols, specific monoalcohols and specific polycarbonates.

The polyols used in the invention are represented by the following general formula [XIX]:

$$R_{22}(OH)_l \qquad \ldots [XIX]$$

wherein R$_{22}$ is an aliphatic hydrocarbon group having 4 to 300 carbon atoms, an aliphatic hydrocarbon group containing an ether bond and having 4 to 300 carbon atoms or a cyclic hydrocarbon group containing an ether bond and having 6 to 300 carbon atoms, and 1 is an integer of 2 to 8.

The polyols represented by the above-mentioned general formula [XIX] include concretely glycols such as diethylene glycol, triethylene glycol, tetraethylene glycol, polyethylene glycol, dipropylene glycol, tripropylene glycol and polypropylene glycol; diols obtained by copolymerization of ethylene oxide and propylene oxide; pentaerythritol, dipentaerythritol, trimethylolpropane, neopentyl glycol and hexylene glycol; polyols consisting of reaction products of pentaerythritol, dipentaerythritol, timethylolpropane, neopentyl glycol or hexylene glycol with ethylene oxide or propylene oxide; polyols consisting of reaction products of propylene oxide or ethylene oxide with hydroxymethyl ethylene oxide or glycerol; pyranose such as glycopyranose, galactopyranose or mannopyranose; and furanose such as fructofuranose or ribofuranose. In addition to those exemplified above, there may also be used dibutylene glycol, tributylene glycol and polybutylene glycol.

The monoalcohols used in the invention are represented by the following general formula [XX]:

$$R_{23}OH \qquad \ldots [XX]$$

wherein $R_{23}$ is a hydrocarbon group having not more than 30 carbon atoms or a hydrocarbon group containing an ether bond and having 2 to 30 carbon atoms.

The hydrocarbon group represented by $R_{23}$ in the general formula [XX] above, includes aliphatic hydrocarbons, alicyclic hydrocarbons, aromatic hydrocarbons, aromatic aliphatic hydrocarbons, and glycol ethers represented by the following general formula:

$$(\!-\!R_{26}\!-\!O\!)_{\overline{q}}R_{27}$$

wherein $R_{26}$ is an alkylene group having 2 to 3 carbon atoms, $R_{27}$ is a hydrocarbon group having not more than 28 carbon atoms, and q is an integer of 1 to 20.

Concrete examples of the hydrocarbon group represented by $R_{23}$ mentioned above are the same as those of the hydrocarbons such as aliphatic hydrocarbons, alicyclic hydrocarbons, aromatic hydrocarbons and glycol ethers enumerated in the case of $R_2$ representing said hydrocarbons as aforementioned.

When the polycarbonates of the invention as illustrated above are used as lubricant oils for refrigerators using an ozone layer-nondestructive Freon such as Freon R-134a as a refrigerant, the above-mentioned $R_{23}$ includes preferably lower alkyl groups such as methyl, ethyl, isopropyl and n-butyl and alkylene glycol monoalkyl ethers such as ethylene glycol monomethyl ether, diethylene glycol monomethyl ether, triethylene glycol monomethyl ether, propylene glycol monomethyl ether, dipropylene glycol monomethyl ether and triproDylene glycol mono-n-butyl ether.

The carbonate used as a starting carbonate in the invention is represented by the following general formula [XXI]:

$$R_{24}OCOOR_{24} \qquad \ldots [XXI]$$

wherein $R_{24}$ are each independently an alkyl group having 1 to 2 carbon atoms.

The carbonate represented by the general formula [XXI] includes concretely dimethyl carbonate, diethyl carbonate and ethyl methyl carbonate, which are easily available.

In the process of the invention for preparing the polycarbonates, there are prepared such polycarbonates as represented by the above-mentioned general formula [XVIII] using the polyols, monoalcohols and carbonates as exemplified above.

In the general formula [XVIII], $R_{22}$ and 1 are as defined in the following general formula [XIX], and $R_{23}$ is as defined in the following general formula [XX].

First, a mixture comprising (a) a polyol represented by the general formula [XIX]:

$$R_{22}(OH)_l \qquad \ldots [XIX],$$

(b) a monoalcohol represented by the general formula [XX]:

$$R_{23}OH \qquad \ldots [XX],$$

and (c) a carbonate represented by the general formula [XXI]:

$$R_{24}OCOOR_{24} \qquad \ldots [XXI],$$

the resulting $R_{24}OH$ from said carbonate during the course of reaction with said polyol being lower in boiling point than said polyol and monoalcohol, and said carbonate being used in such an amount that the ratio of the number of mols of the carbonate to 1-times the number of mols ($1m_5$) of the polyol is 2 to 200, is heated in the presence of a basic catalyst, and the mixture is allowed to undergo reaction so as to proceed to a reaction ratio of not less than 95%, while distilling off the resulting alcohol ($R_{24}OH$) out of the reaction system.

In the above-mentioned $1m_5$, 1 represents the number of hydroxyl groups of the polyol.

In carrying out the reaction, it is desirable that the reactor used therefor is nitrogen purged, though this is not essential thereto.

Subsequently, after removal of the above-mentioned basic catalyst, the unreacted carbonate and the carbonate which has not participated in the final stage reaction [$R_{25}OCO_2R_{25}$ wherein $R_{25}$ are each independently $R_{23}$ or $R_{24}$ as defined above] are distilled off out of the reaction system to obtain the polycarbonates represented by the above-mentioned general formula [XVIII].

According to this process, the carbonation reaction is allowed to proceed, while distilling off the alcohol resulting therefrom out of the reaction system, hence the alcohol resulting from this reaction must be lower in boiling point than the above-mentioned polyol and monoalcohol.

The carbonate of the general formula [XXI] is used in such an amount that the ratio of the number of mols of the carbonate to 1-times the number of mols ($1m_5$) of the polyol is 2 to 200, preferably 3 to 50. By using the limited amount of the starting carbonate in the manner as defined above, it is possible to inhibit the formation of polycarbonates of high polymerization degree.

In the process mentioned above, the reaction is carried out by heating the above-mentioned polyol, monoalcohol and carbonate charged in the reactor in the presence of the basic catalyst, and allowing the charge to undergo reaction so as to proceed to a reaction ratio of not less than 95%, while distilling off the resulting alcohol out of the reaction system. After removal of the basic catalyst, the unreacted carbonate and the carbonate which has not participated in the final stage reaction ($R_{25}OCO_2R_{25}$ wherein $R_{25}$ are each independently $R_{23}$ or $R_{24}$) are then distilled off out of the reaction system. The term "the reaction ratio of not less than 95%" as used herein signifies that the reaction is allowed to proceed until the above-mentioned alcohol is formed at least 0.95 times the number of mols of $1m_5$.

With respect to the above-mentioned basic catalyst, reaction temperature, reaction time, removal of the catalyst after completion of the reaction, removal of impurities from the reaction product and recovery of the unreacted dimethyl carbonate, the above-mentioned process is carried out in the same manner as in the process for preparing the polycarbonates represented by the general formula [I] and [II] as mentioned previously.

According to this process as illustrated above, after removal of the basic catalyst, the unreacted carbonate is distilled off from "the reaction system, thereby inhibiting polymerization of the unreacted carbonate at the time of distilling off the unreacted carbonate in the presence of the basic catalyst, and thus it is possible to obtain the desired polycarbonates in high yields.

Further, by subjecting the polycarbonates thus obtained to adsorption treatment with such adsorbent as activated clay or activated charcoal, trace amounts of ionic compounds or polar compounds are absorbed from the thus obtained polycarbonates, hence the thus treated polycarbonates can be maintained stably.

The polycarbonates prepared by the above-mentioned process according to the present invention may include, for example, those enumerated below.

(1) Tripropylene glycol-di-[2-ethylhexyl]carbonate,
(2) Tripropylene glycol-di-[1,3-dimethylpropyl]carbonate,
(3) Neopentyl glycol-di-[2-ethylhexyl]carbonate,
(4) Neopentyl glycol-di-[n-heptyl]carbonate,
(5) Pentaerythritol-tetra-[n-butyl]carbonate,
(6) Dipropylene glycol-di-[2-ethylhexyl]carbonate,
(7) Sucrose-hexa-[n-butyl]carbonate,
(8) 2,2-Diethylpropanediol-di-[2-ethylhexyl]carbonate,
(9) 2-Methyl-2-ethylpropanediol-di-[2-ethylhexyl]carbonate,
(10) 3-Methylpentadiol-di-heptyl carbonate.

The process for purifying the polycarbonates of the present invention is illustrated below.

The process for purifying the polycarbonates of the invention is applied to the polycarbonates prepared in the presence of basic catalysts, which contain basic substances (basic catalysts, basic substances derived from the basic catalysts).

The polycarbonates containing such basic substances as mentioned above may be prepared by any of the following three processes.

(1) Polyalkylene glycol and a carbonate are allowed to undergo reaction by heating in the presence of a basic catalyst at atmospheric pressure or under reduced pressure, while distilling off the resulting alcohol out of the reaction system.

In carrying out the above reaction, a monoalcohol may be allowed to exist in the reaction system.

Subsequently, after removal by distillation of the unreacted carbonate out of the reaction system, the reaction mixture is heated under reduced pressure to undergo condensation polymerization, and the basic catalyst remaining in the reaction product is neutralized with acid.

In carrying out the above-mentioned reaction, it is desirable that the reactor used therefor is nitrogen purged, though this is not essential thereto.

Examples of the polyalkylene glycol used above include those represented by the following general formula [XXII]:

HO—$R_{28}$—OH                      ... [XXII]

wherein $R_{28}$ is a polyalkylene glycol residue represented by

—$(C_mH_{2m}O)_aC_mH_{2m}$— wherein m is an integer of 1 to 10, and a is an integer of 1 to 100.

The polyalkylene glycol represented by the above-mentioned general formula [XXII] is concretely the same as the polyol represented by the general formula [XIX] mentioned previously.

Examples of the carbonate used above include those represented by the following general formula [XXIII]:

$R_{29}OCOOR_{29}$                      ... [XXIII]

wherein $R_{29}$ is a methyl or ethyl group.

The carbonates of the general formula [XXIII] include concretely dimethyl carbonate and diethyl carbonate. These carbonates are used in such an amount that $m_6/(2m_7+m_8)$ molar ratio is 0.6 to 5, preferably 1 to 3, wherein $m_6$ is the number of mols of carbonate, $m_7$ is the number of the number of moles of polyalkylene glycol, and $m_8$ is the number of mols of the monoalcohol represented by the following general formula [XXIV]. The molar ratio mentioned above may be 0.5 theoretically, however, the terminal hydroxyl group remains in the resulting polycarbonate when the above-mentioned carbonate is not used in excess. Further, the use of the above-mentioned carbonate in large amounts is not economical.

Examples of the above-mentioned monoalcohol used include those represented by the following general formula [XXIV]:

$R_{30}OH$                      ... [XXIV]

wherein $R_{30}$ is an alkyl group having 2 to 20 carbon atoms, an aryl group having 6 to 20 carbon atoms or the group represented by the formula $R_{31}(OC_nH_{2n})_b$— wherein $R_{31}$ is an alkyl group having 1 to 20 carbon atoms, or an aryl group having 6 to 20 carbon atoms, n is an integer of 1 to 10, and b is an integer of 1 to 100.

Preferably useful monoalcohols represented by the above-mentioned general formula [XXIV] include concretely monoalkyl ethers of ethylene glycol, diethylene glycol, triethylene glycol, polyethylene glycol, etc., and monoalkyl ethers of propylene glycol, dipropylene glycol, tripropylene glycol, polypropylene glycol, etc. Particularly preferred alkyl group mentioned above as $R_{30}$ and $R_{31}$ are, for example, methyl and butyl.

Further, ethanol, propanol, butanol, pentanol, hexanol, tridecanol, cyclohexanol, cyclohexylmethanol, phenol and cresol may also be used as the monoalcohol.

The polyalkylene glycol of the general formula [XXII] and the monoalcohol of the general formula [XXIV] are used in such an amount that the molar ratio of monoalcohol/polyalkylene glycol is usually 0 to 2.

When the above-mentioned reaction is carried out using a reactor equipped with a distillation column, the resulting alcohol $R_{29}OH$ can be distilled off efficiently. The above-mentioned carbonate of the formula [XXIII] may be fed in its total amount to the reactor at the initial stage of reaction, or only a part of the carbonate may be fed at the initial stage of reaction, followed by intermittent or continuous addition of the remainder during the reaction.

According to the process of the invention as mentioned above, the reaction is carried out in two steps. The first reaction step of this process comprises feeding the above-mentioned polyalkylene glycol and carbonate (together with a monoalcohol, if necessary) to the reactor, heating the mixture at atmospheric pressure or under pressure in the presence of a basic catalyst, while distilling off the resulting alcohol $R_{29}$ out of the reaction system, and allowing the carbonation reaction to proceed to a reaction ratio of not less than 95%, followed by distilling off the unreacted carbonate out of the reaction system. The reaction ratio of not less than 95% signifies that the reaction is allowed to proceed until the resulting alcohol as mentioned above is formed in an amount of not less than $0.95\times(2m_7+m_8)$ mols.

The second reaction step of the above-mentioned process of the invention comprises heating the thus obtained reaction mixture under reduced pressure, allowing the mixture to undergo condensation polymerization while distilling off the carbonate resulting from the carbonate interchange reaction out of the reaction system, followed by neutralizing the basic catalyst remaining in the reaction product with acid.

With respect to the above-mentioned basic catalyst used herein, the above-mentioned process of the invention is carried out in the same manner as in the process for preparing the polycarbonates represented by the general formulas [I] and [II] as mentioned previously.

The basic catalysts are used in this process in such an amount that the ratio of the number of mols of the catalyst/$(2m_7+m_8)$ is usually $10^{-1}$ to $10^{-7}$, preferably $10^{-2}$ to $10^{-5}$.

In the process of the invention as mentioned above, the first step reaction is the carbonation reaction and the second step reaction is the carbonate interchange reaction, as mentioned above. The carbonation reaction is carried out at a temperature of 50° to 300° C., preferably 60° to 200° C. and atmospheric pressure to 30 kg/cm² preferably atmospheric pressure to 10 kg/cm². The reaction time employed is usually 0.5 to 200 hours, preferably 1 to 100 hours. The carbonate interchange reaction is carried out under a reduced pressure of usually 400 to 1 mm Hg, preferably 200 to 5 mm Hg and at a temperature of 50° to 300° C., preferably 60° to 200° C. The reaction time employed is usually 0.1 to 100 hours, preferably 0.2 to 50 hours.

For neutralizing the catalyst after completion of the reaction, there are used solid acids, inorganic acids and organic acids. For example, the acids used therefor include sulfonic acid type ion exchange resins, carbonic acid, ammonium carbonate, ammonium chloride, hydrochloric acid, sulfuric acid, phosphoric acid, acetic acid and phenol. Of these acids, preferably used are weak acids such as sulfonic acid type ion exchange resins, carbonic acid, ammonium carbonate and ammonium chloride, and the neutralization of the catalyst is effected preferably with an aqueous solution of the weak acid as mentioned above.

According to the process of the invention as illustrated above, there can be obtained polyalkylene glycol polycarbonates having molecular terminals consisting substantially of hydrocarbon groups only.

The polyalkylene glycol polycarbonates thus obtained are represented by the following general formula [XXV]:

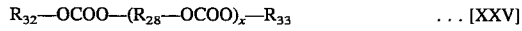

$$R_{32}\text{—OCOO—}(R_{28}\text{—OCOO})_x\text{—}R_{33} \qquad \ldots \text{[XXV]}$$

wherein $R_{28}$ is the same as $R_{28}$ in the general formula [XXII], $R_{32}$ and $R_{33}$ are each independently R30 in the general formula [XXIV] mentioned previously or $R_{29}$ in the general formula [XXIII] mentioned previously, and the average value of x is 0.5 to 10.

When dimethyl carbonate is used as the carbonate in the first step reaction of the above-mentioned process of the invention, an azeotrope former such as cyclohexane, benzene or hexane may be added to the reaction system before initiation of the reaction, whereby methanol produced during the reaction may be removed from the reaction system as an azeotropic mixture with the azeotrope former instead of removing the methanol as an azeotropic mixture with dimethyl carbonate. The azeotrope former is usually used in an amount of 5 to 100% by weight based on the dimethyl carbonate.

According to this process of the invention, methanol resulting from the carbonation reaction can be removed out of the reaction system as an azeotropic mixture with the above-mentioned azeotrope former, and the unreacted dimethyl carbonate can be recovered, after completion of the reaction, from the reaction mixture, thus the recovery of the unreacted dimethyl carbonate can be increased.

Furthermore, there is another procedure in which methanol is recovered as described above as an azeotropic mixture with dimethyl carbonate, the azeotrope former as mentioned above is then added to the azeotropic mixture thus recovered, and the methanol is removed as an azeotropic mixture with the azeotrope former from the dimethyl carbonate, thereby recovering the dimethyl carbonate.

(2) Polyol and a carbonate are allowed to undergo reaction by heating in the presence of a basic catalyst, while distilling off the resulting alcohol out of the reaction system.

In carrying out the above reaction, it is desirable that the reactor used therefor is nitrogen purged, though this is not essential thereto.

Examples of the polyol used in this process include those represented by the following general formula [XXVI]:

$$R_{34}(OH)_j \qquad \ldots \text{[XXVI]}$$

wherein $R_{34}$ is an aliphatic hydrocarbon group having 4 to 300 carbon atoms, which may contain an ether bond, and j is an integer of 2 to 8.

Examples of the carbonate used herein include those represented by the following general formula [XXVII]:

$$R_{35}OCOOR_{35} \qquad \ldots \text{[XXVII]}$$

wherein $R_{35}$ are each an alkyl group having 1 to 20 carbon atoms.

Examples of the carbonate of the general formula [XXVII], which are preferably used in this process, include those enumerated as the examples of the carbonate of the general formula [V] mentioned previously.

In the process of the invention mentioned above, the carbonation reaction is allowed to proceed while distilling off the alcohol resulting from said reaction out of the reaction system, the resulting alcohol represented by $R_{35}OH$ must be lower in boiling point than the above-mentioned polyol.

The carbonate mentioned above is used in such an amount that the $m_9/jm_{10}$ molar ratio is from 2 to 50, preferably 2 to 30, wherein $m_9$ is the number of mols of the carbonate, $m_{10}$ is the number of mols of the polyol, and j is the number of hydroxyl groups of the polyol. By using such a limited amount of the carbonate as defined above, it is possible to inhibit the formation of polycarbonates of high polymerization degree.

In this process, the reaction is carried out by heating the above-mentioned polyol and carbonate fed to a reactor in the presence of a basic catalyst, and the mixture is allowed to undergo reaction so as to proceed to a reaction ratio of not less than 95%, while distilling off the resulting alcohol out of the reaction system. The reaction ratio of not less than 95% signifies that the reaction is allowed to proceed until the resulting alcohol mentioned above is formed at least 0.95 times the molar quantity of $jm_{10}$.

The basic catalyst used herein includes such compounds exemplified as the examples of the basic catalysts used in the process for preparing the polycarbonates represented by the general formulas [I] and [II] mentioned previously. These catalyst are used in such an amount that the ratio of the number of mols of the catalyst/$jm_{10}$ is usually $10^{-1}$ to $10^{-7}$, preferably $10^{-2}$ to $10^{-5}$.

In the process of the invention now described, the reaction is carried out at a temperature usually of 50° to 300° C., preferably 60° to 200° C. and the reaction time employed therefor is usually 0.5 to 200 hours, preferably 1 to 100 hours.

(3) Polyol, monoalcohol and a carbonate are heated in the presence of a basic catalyst, and the mixture is allowed to undergo reaction, while distilling off the resulting alcohol out of the reaction system.

In carrying out the reaction mentioned above, it is desirable that the reactor used therefor is nitrogen purged, though this is not essential thereto.

Examples of the above-mentioned polyol include those represented by the following general formula [XXVIII]:

$$R_{36}(OH)_l \qquad \ldots [XXVIII]$$

wherein $R_{36}$ is an aliphatic hydrocarbon group having 4 to 300 carbon atoms, an aliphatic hydrocarbon group containing an ether bond and having 4 to 300 carbon atoms or a cyclic hydrocarbon group containing an ether bond and having 6 to 300 carbon atoms, and l is an integer of 2 to 8.

The polyol represented by the general formula [XXVIII] mentioned above includes concretely such compounds exemplified as the concrete examples of the polyol represented by the general formula [XIX] mentioned previously.

Examples of the above-mentioned monoalcohol include those represented by the following general formula [XXIX]:

$$R_{37}OH \qquad \ldots [XXIX]$$

wherein $R_{37}$ is a hydrocarbon group having not more than 30 carbon atoms or a hydrocarbon group containing an ether bond and having 2 to 30 carbon atoms.

Concrete examples of the above-mentioned hydrocarbon group represented by $R_{37}$ include those exemplified as the concrete examples of the hydrocarbon group represented by $R_2$ mentioned previously, for example, aliphatic hydrocarbons, alicyclic hydrocarbons, aromatic hydrocarbons and glycol ethers.

Examples of the above-mentioned carbonate include those represented by the following general formula [XXX-1]:

$$R_{40}OCOOR_{40} \qquad \ldots [XXX-1]$$

wherein $R_{40}$ are each independently an alkyl group having 1 to 2 carbon atoms. The carbonates represented by the general formula [XXX-1] include concretely dimethyl carbonate, diethyl carbonate and ethyl methyl carbonate. These carbonates are easily available.

In the process of the invention mentioned above, the carbonation reaction is allowed to proceed, while distilling off the alcohol resulting from said reaction out of the reaction system, hence the resulting alcohol represented by $R_{40}OH$ must be lower in boiling point than the above-mentioned polyol and monoalcohol.

The carbonate mentioned above is used in such an amount that the molar ratio of the carbonate to l-times the number of mols ($lm_{11}$) of the polyol of the above-mentioned general formula [XXVIII] is 2 to 50, preferably 2 to 30, wherein $m_{11}$ is the number of mols of the polyol and l is the number of hydroxyl groups of the polyol. By using such a limited amount of the carbonate as defined above, it is possible to inhibit the formation of polycarbonates of high polymerization degree.

In this process, the reaction is carried out by heating the above-mentioned polyol, monoalcohol and carbonate fed to a reactor in the presence of a basic catalyst, and the mixture is allowed to undergo reaction so as to proceed to a reaction ratio of not less than 95%, while distilling off the resulting alcohol out of the reaction system. The reaction ratio of not less than 95% signifies that the reaction is allowed to proceed until the resulting alcohol mentioned above is formed in an amount of at least $1m_{11}$ mols.

The above-mentioned basic catalyst used in this process includes such compounds exemplified as the basic catalysts used in the process for preparing the polycarbonates represented by the general formulas [I] and [II] mentioned previously. These catalysts are used in such an amount that the ratio of the number of mols of the catalyst/$1m_{11}$ is usually $10^{-1}$ to $10^{-7}$, preferably $10^{-2}$ to $10^{-5}$.

In this process of the invention, the reaction is carried out at a temperature of usually 50° to 300° C., preferably 60° to 200° C., and the reaction time employed therefor is usually 0.5 to 200 hours, preferably 1 to 100 hours.

The polycarbonates obtained respectively by the above-mentioned processes (1), (2) and (3) contain basic substances.

The process for purifying polycarbonates according to the present invention is directed to the purification of such polycarbonates containing basic substances as mentioned above.

Removal of basic substances from polycarbonates containing the same may be performed by the following three processes.

(1) A process for the removal of basic substances from polycarbonates, which comprises removing the basic substances from the polycarbonates containing the same by washing said polycarbonates with water.

In carrying out this process, it is desirable that the basic substances contained in the polycarbonates is neutralized with an aqueous weak acid solution, and the polycarbonates are then washed with water.

Useful aqueous weak acid solutions in this process include those of inorganic acids such as ammonium carbonate, carbonic acid, ammonium chloride, etc.

In that case, if necessary, a non-polar solvent may be added to the polycarbonates containing the basic substances prior to subjecting them to such removal treatment as mentioned above.

The non-polar solvent referred to above includes concretely aromatic hydrocarbons such as toluene, benzene, xylene, etc., and saturated hydrocarbons such as hexane, octane, etc.

(2) A process for the removal of basic substances from polycarbonates, which comprises bringing the basic substances contained in the polycarbonates into contact with an inorganic ion exchanger.

In this process, if necessary, a non-polar solvent as mentioned in the foregoing process (1) may also be added to the polycarbonates containing the basic substances prior to subjecting said polycarbonates to such removal treatment as mentioned above.

Useful inorganic ion exchangers in this process include concretely zeolite and "IXE inorganic ion exchangers" produced by Toa Gosei Chem. Ind. Co. Ltd., for example, inorganic ion exchangers of the cation exchanger such as GRADE IXE-100 (ingredient: zirconium compound), IXE-300 (ingredient: antimony compound), etc., and inorganic ion exchangers of the amphoteric ion exchanger such as GRADE IXE-600 (ingredients: antimony, bismuth compound). In the present invention, there may also be used as the inorganic ion exchanger such inorganic materials as acid clay and dolomite, but they are low in ion exchange ability.

As is well known, the ion exchangers include inorganic ion exchangers and organic ion exchangers, but an organic ion exchanger having a sulfone group as an exchange group is low in ion exchange ability.

(3) A process for the removal of basic substances from polycarbonates containing the same, which comprises employing a combination of the treatment for the removal of basic substances by means of water-washing as described in the foregoing (1) with the treatment for the removal of basic substances by means of an inorganic ion exchanger.

In this process, the above-mentioned treatment (1) may first be carried out followed by the above-mentioned treatment (2), or the treatment (2) may first be carried out followed by the treatment (1).

In the present invention, it is desirable that the basic substances are removed from the polycarbonates containing the same by the above-mentioned process (1) or (3), followed by dehydration treatment.

EFFECT OF THE INVENTION

The first and second polycarbonates of the present invention, that is, those represented by the general formulas [I] and [II] as mentioned previously, are excellent in lubricating properties and detergency and, at the same time, excellent in compatibility, though they are highly viscous, with an ozone layer-nondestructive HFC such as Freon R-134a or 152a, a hydrogenated chlorofluorocarbon (HCFC) having a small ozone-destructive ability such as Freon R-22, R-123 or R-124 or mixtures thereof. Of the polycarbonates of the invention, even those having a high kinematic viscosity at 100° C. as high as 15 cSt or more are also excellent in compatibility with Freon R-134a.

The first and second polycarbonates of the invention having such effect as mentioned above may be used as lubricant oils for refrigerators wherein an ozone layer-nondestructive Freon R-134a is used as a refrigerant, for example, a lubricant oil for rotary car air conditioners, and also as lubricant oils for refrigerators wherein a conventional Freon is used as a refrigerant, automotive engine oils, automotive gear oils, rolling lubricant oils and lubricant oils for fibers.

The third and fourth polycarbonates of the invention, that is, those represented by the general formulas [VIII] and [XIII] as mentioned previously, are excellent in compatibility with Freons as mentioned above as well as in lubricating properties and detergency.

The third and fourth polycarbonates of the invention having such effects as mentioned above are capable of providing lubricant oils for refrigerators, automotive engine oils, automotive gear oils, rolling lubricant oils and lubricant oils for fibers, and lubricant oils and electrical insulating oils for which particularly electrical insulation properties are required. The polycarbonates of the invention are suitable for use in lubricant oils for refrigerators wherein an ozone layer-nondestructive HFC, a Freon (HCFC) having a small ozone-destructive ability or a mixture thereof is used as a refrigerant, or in lubricant oils and electrical insulating oils for electric refrigerators.

According to the process for preparing the polycarbonates of the present invention, after completion of the reaction of polyol with carbonate, the basic catalyst used is removed from the reaction mixture, followed by removal of unaltered carbonate, and hence it is possible to obtain polycarbonates.

In the present invention, moreover, when the polycarbonates are prepared, there is no need for preparing the starting carbonate compound in advance, because the carbonate compound used in the invention is dimethyl carbonate, diethyl carbonate or ethyl methyl carbonate which is easily available. Accordingly, in accordance with the present invention, there can be prepared polycarbonates with economy.

In accordance with the process for purifying polycarbonates of the present invention, there can be obtained polycarbonates of such high purity that the amount of a residual base is not more than 0.1 ppm and the total acid value is less than 1.

The present invention is illustrated below with 0 reference to examples, but it should be construed that the invention is in no way limited to those examples. In the following examples, the results of analysis and evaluation of performance of the polycarbonates were obtained by the following test methods.

(1) Analytical method a. Average molecular weight

Using a GPC system of Shimadzu Seisakusho Ltd., the average molecular weight of the polycarbonate obtained was determined on the basis of polystyrene. The conditions under which the average molecular weight was determined are as follows.

Column: Four (4) pieces of polystyrene gel (G-2000HXL+G-2000HXL+G-3000HXL+G-4000HXL)

Sensor: Differential refractometer

Solvent: Tetrahydrofuran

Rate of elution: 0.7 ml/min b. Infrared absorption spectrum

The determination is conducted using the specimen spread between KBr plates by means of an infrared spectrometer manufactured and sold by Nippon Bunkoh K.K.

c. NMR analysis

The n value of the formula [E] representing $R_1$ in the general formulas [I] and [II] is obtained by the proton NMR method JNM-GX270 manufactured and sold by Nippon Densi K. K.

(2) Evaluation method a. Kinematic viscosity JIS K-2283 b. Viscosity index JIS K-2283 c. Pour point JIS K-2269 d. Load bearing capacity

After a 5-minute warming-up operation under a load of 50 lbf using a Falex tester, the load is increased continuously, and a value of the increased load obtained, at which burn markings have appeared, is taken as a value of load bearing capacity.

e. Volume resistivity

A volume resistivity of the polycarbonate obtained was determined in accordance with ASTM D 257.

f. Compatibility with Freon R-134a (1) A test tube of 10 mm in inside diameter and 20 cm in depth is charged with 1 ml of the specimen and, while cooling the test tube on a dry ice/acetone bath, Freon R-134a is introduced gradually into the test tube from a bomb and stored so as to reach a volume slightly larger than that of the specimen. The mixture in the test tube is then stirred by means of a spatula, and the test tube is transferred onto a cooling bath kept at −20° C. to investigate a solubility of the specimen in Freon R-134a at the time when the volume ratio of the specimen/Freon R-134a has become 1/1. At the time of the investigation, when the resulting mixture is a perfectly homogeneous solution, the rating is taken as o, and when the specimen does not dissolve in Freon R-134a, the rating is taken as x.

(2) In order to investigate the solubility of the carbonate product in Freon R-134a more in detail, a lubricant and Freon R-134a are encapsulated in various proportions into a glass tube to obtain a critical temperature at which the two compounds become compatible with each other.

EXAMPLE 1

A 5-liter reactor equipped with a distillation column of a 10-sieve tray was charged with 764 g (0.97 mol) of a propylene oxide adduct of sucrose having an average molecular weight (Mn) of 740 (SU-460 of PPG-polyfunctional Series, a product of Mitsui Toatsu Chem. Inc.), 2370 g (26.33 mol) of dimethyl carbonate and 0.73 g (0.004 mol in terms of $NaOCH_3$) of a methanol solution of 28% by weight of $NaOCH_3$.

The resulting mixture was heated at 110°–120° C. at atmospheric pressure to carry out reaction while distilling off the resulting methanol as an azeotropic mixture with dimethyl carbonate, whereby the effusion of the methanol ceased after 9.0 hours. The amount of the methanol formed was 189 g (5.0 mol), and the yield of the methanol was about 100%.

The reaction mixture thus obtained was charged with hexane and, the catalyst was neutralized with an aqueous solution containing ammonium carbonate in an amount of five times the molar quantity of the $NaOCH_3$ used. The reaction mixture thus treated was washed with water, and the hexane and unaltered dimethyl carbonate were removed from said reaction mixture containing the same to obtain 1067 g of a polycarbonate.

The polycarbonate thus obtained is a viscous liquid, and from the results of $^1$H-NMR, $^{13}$C-NMR, IR and GPC analysis, it was found that the polycarbonate has a structure represented by the following formula.

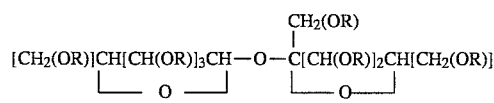

wherein R is $—[CH_2CH(CH_3)O]_n COOCH_3$ in which n=0–3, and an average value of n is about 1.1.

The polycarbonate obtained was analyzed by means of $^{13}$C-NMR, whereby such peaks as mentioned below appeared in the chart. In this case, $CDCl_3$ was used as the solvent therefor.

16–17 ppm, 54–55 ppm, 66–67.5 ppm, 69–70 ppm, 70–72 ppm, 72–73 ppm, 73–74 ppm, 74–76 ppm, 76.5–78 ppm, 78–79 ppm, 79–80 ppm, 80–81.5 ppm, 81.5–83 ppm, 83–85 ppm, 88–90 ppm, 103–105 ppm, 154–155 ppm The infrared absorption spectrum of the polycarbonate obtained are shown in FIG. 1, wherein the main peaks observed are as in the following.

vC-H 2800–3000 $cm^{-1}$

δC-H 1440 $cm^{-1}$ vC=O 1745 $cm^{-1}$ vC-O 1250–1290 $cm^{-1}$ vC-O-C 1100 $cm^{-1}$

The results of GPC analysis of the polycarbonate obtained are shown below.

Weight-average molecular weight (Mw)/number-average molecular weight (Mn) GPC: 1.51

Weight-average molecular weight measured by the polystyrene conversion method: 1337

Amount of sodium remaining in the product: Not more than 0.01 ppm

Total acid value in the product: Not more than 0.01

Results of evaluation of fundamental performance as lubricating oil are shown in Table 1.

EXAMPLE 2

The same procedure as described in Example 1 was repeated to obtain 526 g of a polycarbonate, except that 352 g (0.44 mol) of a propylene oxide adduct of sucrose (SC-800, a product of Asahi Denka K. K.) having an average molecular weight of 800 was used instead, and the amounts of the dimethyl carbonate and the methanol solution containing 28% by weight of $NaOCH_3$ used were changed to 1632 g (18.12 mol) and 0.3 g (0.0016 mol in terms of $NaOCH_3$), respectively.

The amount and yield of methanol as formed were 111.9 g (3.49 mol) and 99% respectively.

The polycarbonate thus obtained was viscous liquid, and from the results of $^{13}$C—NMR, IR and GPC analysis it was found that the polycarbonate has a structure represented by the following formula.

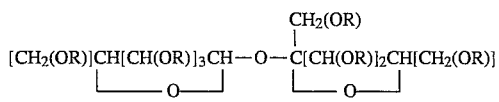

wherein R is $—[CH_2CH(CH_3)O]_n COOCH_3$ in which n=0–3, and an average value of n is about 1.3.

The polycarbonate obtained was analyzed by means of $^{13}$C-NMR, whereby such peaks as mentioned below appeared in the chart. In this case, $CDCl_3$ was used as the solvent therefor.

16–17 ppm, 54–55 ppm, 66–67.5 ppm, 69–70 ppm, 70–72 ppm, 72–73 ppm, 73–74 ppm, 74–76 ppm, 76.5–78 ppm, 78–79 ppm, 79–80 ppm, 80–81.5 ppm, 81.5–83 ppm, 83–85 ppm, 88–90 ppm, 103–105 ppm, 154–155 ppm Data of the infrared absorption spectrum of the polycarbonate obtained are shown in FIG. 1, wherein the main peaks observed are as in the following.

vC-H 2800–3000 $cm^{-1}$

δC-H 1445 $cm^{-1}$ vC=O 1740 $cm^{-1}$ vC-O 1240–1295 $cm^{-1}$ vC-O-C 1100 $cm^{-1}$

The results of GPC analysis of the polycarbonate obtained are shown below.

Weight-average molecular weight (Mw)/number-average molecular weight (Mn) GPC: 1.43

Weight-average molecular weight (Mw) measured by the polystyrene conversion method: 1076

Amount of sodium remaining in the product: Not more than 0.01 ppm

Total acid value in the product: Not more than 0.01

Results of evaluation of fundamental performance as lubricating oil are shown in Table 1.

EXAMPLE 3

The same reactor as used in Example 1 was charged with 377 g of a propylene oxide adduct of sucrose having an average molecular weight (Mn) of 580 (SU-450M of PPG-Polyfunctional Series, a product of Mitsui Toatsu Chem. Inc.), 901 g of isopropanol, 1351 g of dimethyl carbonate and 2 g of a methanol solution containing 28% by weight of $NaOCH_3$.

The mixture thus charged was allowed to undergo reaction at atmospheric pressure at 90°–140° C. for 18 hours.

After removal of the catalyst from the reaction mixture thus obtained, diisopropyl carbonate was distilled off to obtain 570 g of a polycarbonate.

The polycarbonate thus obtained was viscous liquid, and from the results of $^{13}C$—NMR, IR and GPC analysis it was found that the polycarbonate has a structure represented by the following formula.

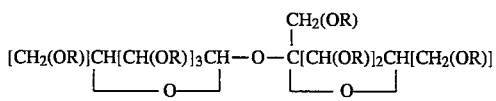

wherein R is $—[CH_2CH(CH_3)O]_nCOOCH(CH_3)_2$, in which n=0–3, and an average value of n is about 1.1.

The polycarbonate obtained was analyzed by means of $^{13}C$-NMR, whereby such peaks as mentioned below appeared in the chart. In this case, $CDCl_3$ was used as the solvent therefor.

16–18 ppm, 21–22 ppm, 54–55 ppm, 71–72 ppm, 74–75 ppm, 74.5–75.5 ppm, 76.5–78 ppm, 89–90 ppm, 104–105 ppm Data of the infrared absorption spectrum of the polycarbonate obtained are shown in FIG. 1, wherein the main peaks observed are as in the following.

νC-H 2800–3000 $cm^{-1}$

δC-H 1450 $cm^{-1}$

νC=O 1740 $cm^{-1}$

νC-O 1240–1290 $cm^{-1}$

νC-O-C 1100 $cm^{-1}$

The results of GPC analysis of the polycarbonate obtained are shown below.

Weight-average molecular weight (Mw)/number-average molecular weight (Mn) [GPC]:1.48

Weight-average molecular weight (Mw) measured by the polystyrene conversion method:2736

Amount of sodium remaining in the product: Not more than 0.01 ppm

Total acid value in the product: Not more than 0.01

Results of evaluation of fundamental performance as lubricating oil are shown in Table 1.

EXAMPLE 4

The same reactor as used in Example 1 was charged with 402 g of a propylene oxide adduct of sucrose having an average molecular weight (Mn) of 740 (SU-460 of PPG-Polyfunctional Series, a product of Mitsui Toatsu Chem. Inc.), 400 g of polypropylene glycol (molecular weight 2,000), 805 g of n-butanol, 980 g of dimethyl carbonate and 0.9 g of a methanol solution containing 38% by weight of $NaOCH_3$.

The mixture thus charged was allowed to undergo reaction at atmospheric pressure at 110°–160° C. for 18 hours.

After removal of the catalyst from the reaction mixture thus obtained by the addition thereto of water, dibutyl carbonate was distilled off to obtain 997 g of a polycarbonate having a structure represented by the following formula.

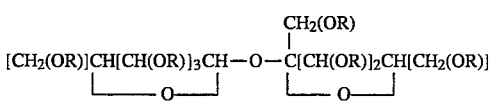

wherein R is $—[CH_2CH(CH_3)O]_nCOOC_4H_9$, in which n=0–3, and an average value of n is about 1.1.

Results of evaluation of fundamental performance as lubricating oil are shown in Table 1.

TABLE 1

|  | Example 1 | Example 2 | Example 3 | Example 4 |
|---|---|---|---|---|
| Viscosity characteristics 100° C. kinematic viscosity [cSt] | 30.9 | 24.8 | 68 | 34 |
| Load bearing capacity [lbf] | 860 | 830 | 880 | 920 |
| Compatibility with Freon R-134a (Note 1) | o | o | o | o |
| Critical temperature [°C.] (Note 2) | | | | |
| High-temperature side | +85 | +82 | +81 | +47 |
| Low-temperature side | <−65 | <−65 | <−65 | <−65 |

(Note 1)
o: Compatible
x: Not Compatible
(Note 2)
Lubricating oil: 15% by weight
Freon R-134a: 85% by weight Lubricating properties of the polycarbonates as prepared in Examples 1–4 evaluated on the basis of the compatibility of said polycarbonates with Freon R-134a and load bearing capacity of said polycarbonates were excellent.

EXAMPLE 5

A car air-conditioner (TV-12EC, a product of Nippon Denso Co. ,Ltd. ) was started by an electric motor (2,000 rpm) using 120 cc of the polycarbonate of Example 4 as an oil for refrigerator and 700 g of Freon R-134a (HFC) as a refrigerant, whereupon it was possible to carry out the airconditioning operation as is evident from the data shown in Table 2. In this case, the outdoor temperature was 23° C.

REFERENTIAL EXAMPLE 1

Example 5 was repeated exactly in the same manner, except that in place of the polycarbonate of Example 4, a commercially available oil for refrigerator (Denso Oil-7, a product of Nippon Denso Co., Ltd. ) was used and in place of Freon R-134a (HFC), Freon R-12 (CFC) was used. The results obtained are shown in Table 2. In this case, the outdoor temperature was 23° C.

TABLE 2

|  | Example 5 | Referential Example 1 |
|---|---|---|
| Oil for refrigerator | Polycarbonate | Commercially |

TABLE 2-continued

|  | Example 5 | Referential Example 1 |
|---|---|---|
|  | of Example 4 | available product |
| Refrigerant gas Pressure [kg/cm²] | Freon R-134a | Freon R-12 |
| Intake side | 1.5–2.0 | 1.5 |
| Exhaust side | 25–28 | 17–18 |
| Air current temperature [°C.] |  |  |
| Cooler out | 11–13 | 9–11 |
| Evaporator out | 37–44 | 43–47 |

EXAMPLE 6

Example 1 was repeated to obtain 412 g of a polycarbonate, except that in place of the propylene oxide adduct of sucrose, a propylene oxide adduct of lactose having an average molecular weight of 798 was used.

The polycarbonate thus obtained was a viscous liquid, and from the results of $^{13}$C-NMR, IR and GPC analysis, it was found that the polycarbonate has a structure represented by the formula mentioned below.

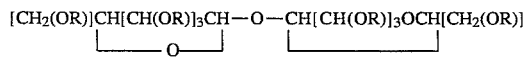

wherein R is —[CH$_2$CH(CH$_3$)O]$_n$COOCH$_3$, in which n=0–3, and an average value of n is about 1.3.

The compatibility of the polycarbonate thus obtained with Freon R-134a as measured by the test method (1) mentioned in Table 2 was rated o.

EXAMPLE 7

Example 1 was repeated to obtain 386 g of a polycarbonate, except that in place of the propylene oxide adduct of sucrose, a propylene oxide adduct of isomaltose having an average molecular weight of 856 was used.

The polycarbonate thus obtained was viscous liquid, and from the results of $^{13}$C-NMR, IR and GPC analysis, it was found that the polycarbonate has a structure represented by the formula mentioned below.

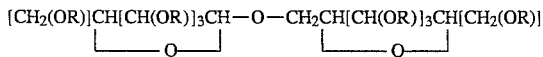

wherein R is —[CH$_2$CH(CH$_3$)O]$_n$COOCH$_3$, in which n=0–3, and an average value of n is about 1.5.

The compatibility of the polycarbonate thus obtained with Freon R-134a as measured by the test method (1) mentioned in Table 2 was rated o.

EXAMPLE 8

Example 1 was repeated to obtain 506 g of a polycarbonate, except that in place of the propylene oxide adduct of sucrose, an addition product of propylene oxide and ethylene oxide of sucrose was used.

The polycarbonate thus obtained was viscous liquid, and from the results of $^{13}$C-NMR, IR and GPC analysis, it was found that the polycarbonate has a structure represented by the formula mentioned below.

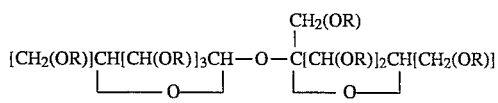

wherein R is —[CH$_2$CH(CH$_3$)O]$_n$[CH$_2$CH$_2$O]$_p$COOCH$_3$ in which n=0–3, an average value of n is 2.2, p=0–3, and an average value of p: about 1.0.

The compatibility of the polycarbonate thus obtained with Freon R-134a as measured by the test method (1) mentioned in Table 2 was rated o.

EXAMPLE 9

Example 1 was repeated to obtain 535 g of a polycarbonate, except that 356 g (0.59 mol) of a propylene oxide adduct of sorbitol (SP-600, a product of Asahi Denka Kogyo K. K.) as a polyol, and the amounts of dimethyl carbonate and the methanol solution of 28% by weight of NaOCH$_3$ used were changed to 1607 g (17.84 mol) and 0.34 g (0.0018 mol in terms of NaOCH$_3$), respectively.

The amount of methanol formed was 110 g (3.44 mol), and the yield of methanol was 97%.

The polycarbonate thus obtained was a viscous liquid, and from the results of $^{13}$C-NMR, IR and GPC analysis, it was found that the polycarbonate has a structure represented by the following formula mentioned below.

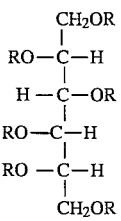

wherein R is —[CH$_2$CH(CH$_3$)O]$_n$COOCH$_3$ in which n=0–3, and an average value of n is about 1.2.

The polycarbonate obtained was analyzed by means of $^{13}$C-NMR, whereby such peaks as mentioned below appeared in the chart. In this case, CDCl$_3$ was used as the solvent therefor.

16–17.5 ppm, 54–55 ppm, 66–68 ppm, 68.5–70 ppm, 70–72 ppm, 72–73 ppm, 73–74.5 ppm, 74.5–76 ppm, 76–78 ppm, 78–79 ppm, 79–80 ppm, 154–156 ppm.

Figure 2:
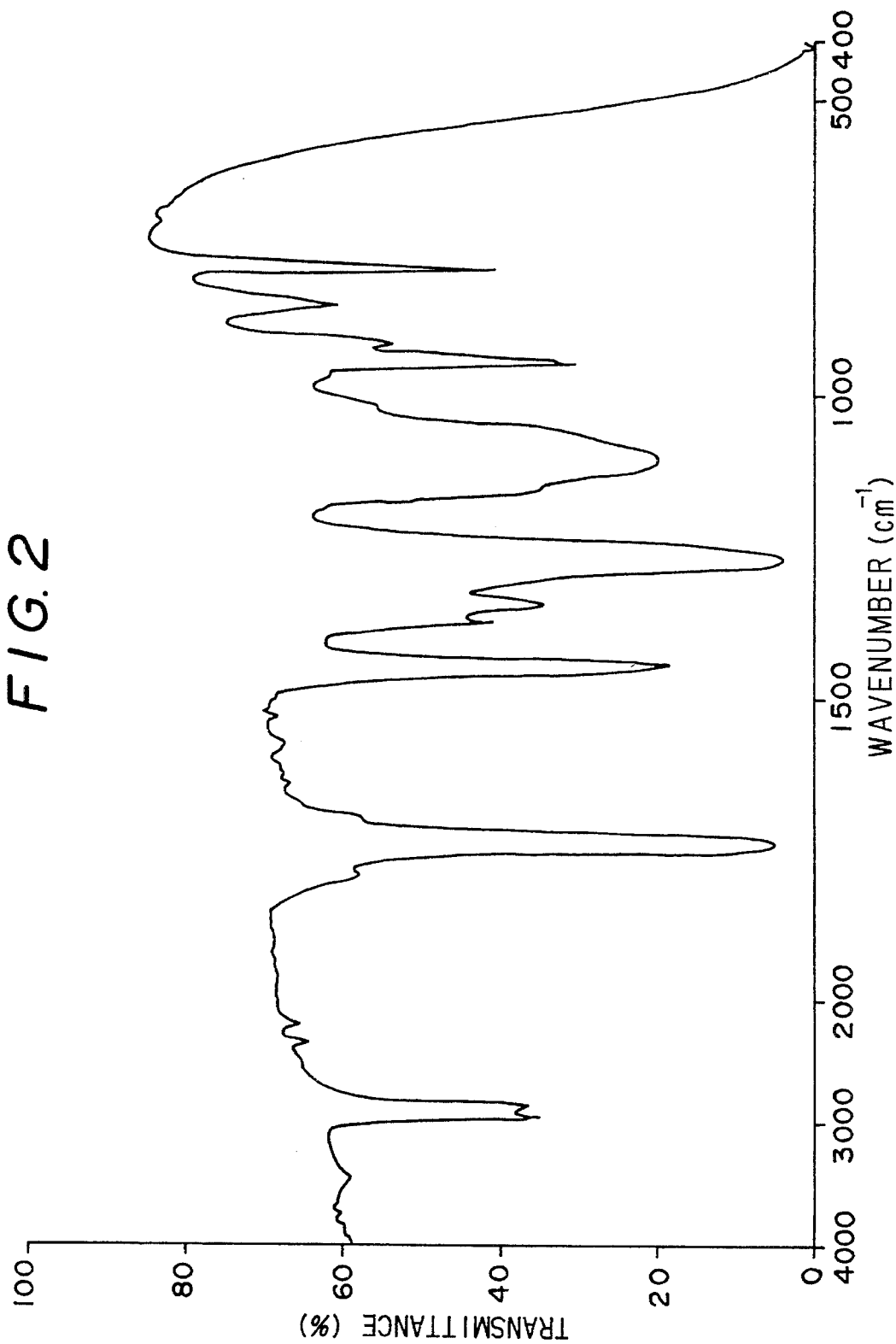

The infrared adsorption spectrum of the polycarbonate obtained is shown in FIG. 2.

The results of GPC analysis of the polycarbonate obtained are shown below.

Weight-average molecular weight (Mw)/number-average molecular weight (Mn) GPC: 1.23

Weight-average molecular weight (Mw) measured by the polystyrene conversion method: 778

Amount of sodium remaining in the product: Not more than 0.01 ppm

Total acid value in the product: Not more than 0.01

Results of evaluation of fundamental performance as lubricating oil are shown in Table 3.

EXAMPLE 10

The same reactor as used in Example 1 was charged with 557 g of a propylene oxide adduct of sucrose having an average molecular weight (Mn) of 1380 (SP-21P, a product of Toho Kagaku Kogyo K. K.), 1747 g of diisopropyl carbonate and 2.1 g of a methanol solution of 28% by weight of $NaOCH_3$.

The resulting mixture was allowed to undergo reaction at atmospheric pressure and 120°–150° C. for 7 hours.

The polycarbonate thus obtained is a viscous liquid, and from the results of $^1$H-NMR, IR and GPC analysis, it was found that the polycarbonate has a structure represented by the formula mentioned below.

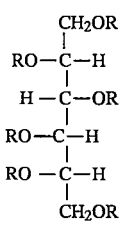

wherein R is $—[CH_2CH(CH_3)O]_nCOOCH(CH_3)_2$, in which n=0, 3–4, and an average value of n is about 3.4.

The polycarbonate obtained was analyzed by means of $^1$H-NMR, whereby such peaks as mentioned below appeared in the chart. In this case, $CDCl_3$ was used as the solvent therefor.

1.1–1.2 ppm, 1.25–1.32 ppm, 3.25–3.45 ppm, 3.45–3.60 ppm, 3.6–3.8 ppm, 4.8–4.9 ppm.

Data of the infrared absorption spectrum of the carbonate obtained are shown below, wherein the main peaks are as shown in the following.

Data of the infrared absorption spectrum of the polycarbonate obtained are shown below, wherein the main peaks observed are as in the following.

vC-H 2800–3000 $cm^{-1}$

δC-H 1450 $cm^{-1}$ vC=O 1740 $cm^{-1}$ vC-O 1240–1290 $cm^{-1}$ vC-O-C 1100 $cm^{-1}$

The results of GPC analysis of the polycarbonate obtained are shown below.

Weight-average molecular weight (Mw)/number-average molecular weight (Mn) GPC: 1.23

Weight-average molecular weight (Mw) measured by the polystyrene conversion method: 2936

Amount of sodium remaining in the product: Not more than 0.01 ppm

Total acid value in the product: Not more than 0.01

Results of evaluation of fundamental performance as lubricating oil of the polycarbonate obtained are shown in Table 3.

EXAMPLE 11

Example 10 was repeated to obtain 867 g of a polycarbonate, except that 700 g of an addition product of propylene oxide and ethylene oxide of sorbitol having an average molecular weight (Mn) of 1530 (SP-21P, a product of Toho Kagaku Kogyo K. K.) was used instead, and the amounts of diisopropyl carbonate and the methanol solution of 28% by weight of $NaOCH_3$ were changed to 2344 g and 14 g, respectively.

The polycarbonate thus obtained was a viscous liquid, and from the result of $^1$H—NMR, IR and GPC analysis, it was found that the polycarbonate has a structure represented by the formula mentioned below.

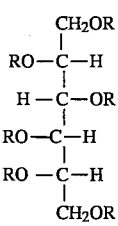

wherein R is $—[CH_2CH(CH_3)O]_n[C_2H_4O]_pCOOCH(CH_3)_2$ in which n= 0–6, an average value of n is about 3.5, p=0–2, and an average value of p is about 1.0.

The polycarbonate obtained was analyzed by means of $^1$H—NMR, whereby such peaks as mentioned below appeared in the chart. In this case, $CDCl_3$ was used as the solvent therefor.

1.1–1.18 ppm, 1.25–1.32 ppm, 3.25–3.45 ppm, 3.45–3.60 ppm, 3.6–3.8 ppm, 4.8–4.9 ppm.

Data of the infrared absorption spectrum of the polycarbonate are shown with reference to the main peaks as mentioned below.

ξC-H 2800–3000 $cm^{-1}$

δC-H 1450 $cm^{-1}$ vC=O 1740 $cm^{-1}$ vC-O 1240–1280 $cm^{-1}$ vC-O-C 1100 $cm^{-1}$

The results of GPC analysis of the polycarbonate obtained are shown below.

Weight-average molecular weight (Mw)/number-average molecular weight (Mn) GPC : 1.29

Weight-average molecular weight (Mw) measured by the polystyrene conversion method: 2989

Amount of sodium remaining in the product: Not more than 0.01 ppm

Total acid value in the product: Not more than 0.01

Results of evaluation of the fundamental performance as lubricating oil of the polycarbonate obtained are shown in Table 3.

EXAMPLE 12

Example 10 was repeated to obtain 1100 g of a polycarbonate, except that 1050 g of polypropylene glycol having a molecular weight of 1500 was used instead, the amounts of diisopropyl carbonate and the methanol solution of 28% by weight of $NaOCH_3$ used were changed to 1533 g and 4 g, respectively, and the reaction temperature and reaction time were changed to 140°–150° C. and 10 hours, respectively.

The polycarbonate thus obtained had a kinematic viscosity at 100° C. of 21 cSt, the compatibility of the polycarbonate with Freon R-134a measured by the aforesaid test method (1) was rated o, and the critical temperature of the polycarbonate as measured by the aforesaid test method (2) was 59° C. at the high temperature side and −65° C. at the low temperature side.

This polycarbonate (A) and the polycarbonate (B) of Example 10 were mixed together in a weight ratio [(A)/(B)] of 25/75 to obtain a polycarbonate having such lubricant characteristics as shown in Table 3.

TABLE 3

|  | Example 9 | Example 10 | Example 11 | Example 12 |
|---|---|---|---|---|
| Viscosity characteristics 100° C. kinematic viscosity [cSt] | 14.2 | 36 | 33 | 30 |
| Load bearing capacity [lbf] | 890 | 910 | 890 | 930 |
| Compatibility with Freon R-134a (Note 1) | o | o | o | o |
| Critical temperature [°C.] (Note 2) | | | | |
| High-temperature side | +96 | +81 | +72 | +71 |
| Low-temperature side | <−65 | <−65 | <−65 | <−65 |

(Note 1)
o: Compatible
x: Not Compatible
(Note 2)
Lubricant: 15% by weight
Freon R-134a: 85% by weight The polycarbonates obtained in Examples 9–12 were all excellent in lubricating properties as defined on the basis of the determined compatibility with Freon R-134a and load bearing capacity.

EXAMPLE 21

The same reactor as used in Example 1 was charged with 301 g (2.89 mol) of neopentyl glycol, 4293 g (15.01 mol) of di-[2-ethylhexyl]carbonate and 1.0 g (NaOCH$_3$ $_{0.005}$ mol) of a methanol solution of 28% by weight of NaOCH$_3$.

The resulting mixture was allowed to undergo reaction for 10 hours under reduced pressure (40–10 mm Hg) by heating at 130°–160° C. while distilling off the resulting 2-ethyl-hexanol. The amount of the distilled 2-ethylhexanol was 742 g (5.70 mol), and the yield of said 2-ethylhexanol was 99%.

The reaction mixture thus obtained was charged with an aqueous solution containing ammonium carbonate in an amount of five times the molar quantity of the NaOCH used to neutralize the catalyst present therein, followed by water washing. Unaltered di-[2-ethylhexyl]carbonate was then removed from the reaction mixture containing the same to obtain 962 g of a polycarbonate.

The polycarbonate thus obtained was a liquid, and from the results of $^1$H—NMR, IR and GC-Ms analysis, it was found that said polycarbonate has a structure represented by the following formula.

$(CH_3)_2C[CH_2COOCH_2CH(C_2H_5)C_4H_9]_2$

The polycarbonate thus obtained was analyzed by means of $^1$H—NMR, whereby such peaks as mentioned below appeared in the chart. In this case, CDCl$_3$ was used as the solvent therefor.

0.87–0.93 ppm (tri 12H), 1.0 ppm (s 6H), 1.25–1.35 ppm (8H), 1.35–1.45 ppm (8H), 1.59–1.65 ppm (2H), 3.97 ppm (s 4$_H$), 4.0–4.08 ppm (4H)

On GC-Ms analysis of this polycarbonate, a molecular ion peak of M$^+$ appeared at m/e=417 in the chart.

Figure 3:
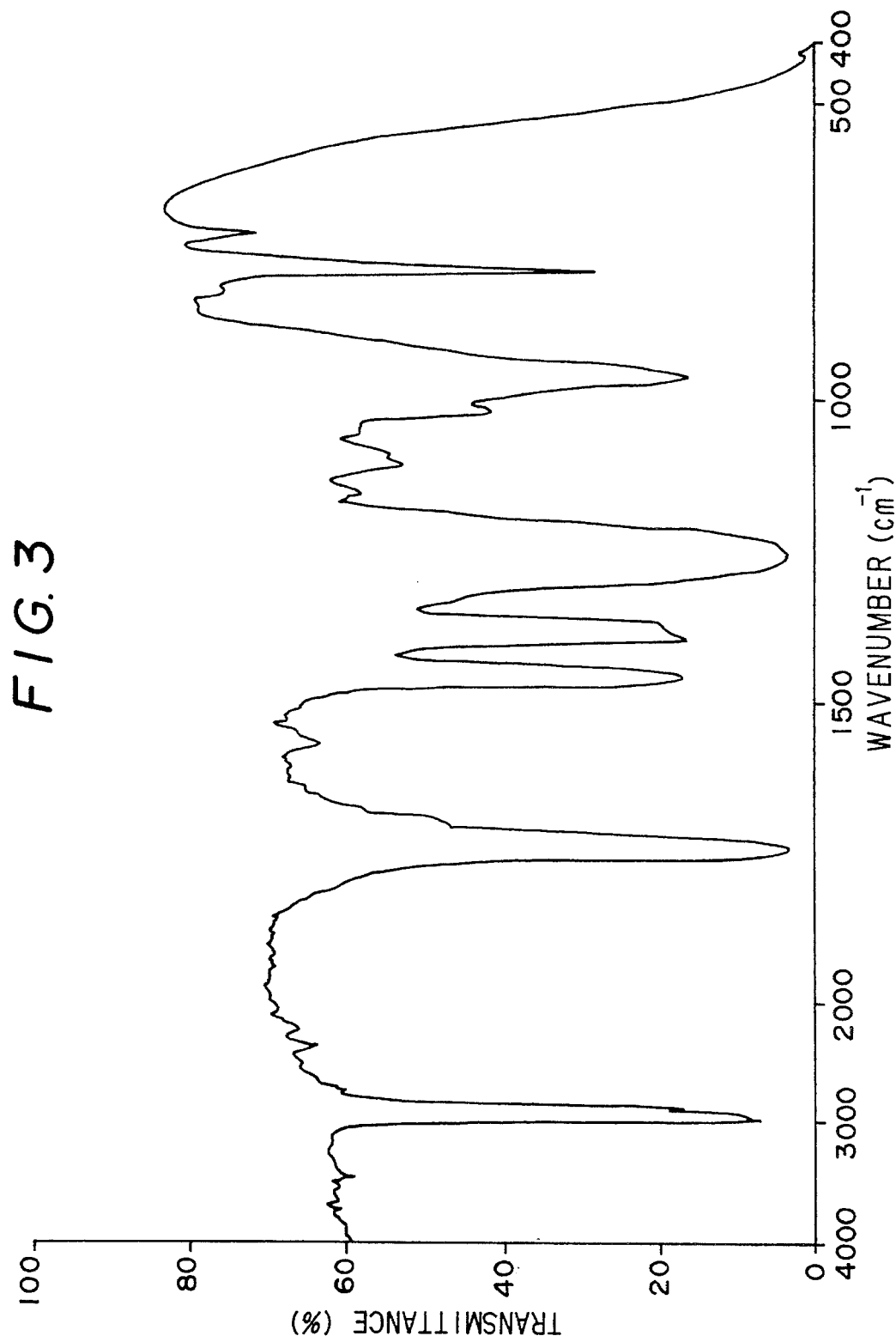

The infrared absorption spectrum of the polycarbonate thus obtained are shown in FIG. 3.

The results of GPC analysis of the carbonate obtained are shown below. In that case, it was confirmed that a condensate of pentyl-di-[2-ethylhexyl]carbonate partly exists in the resulting product.

Weight average molecular weight (Mw)/number average molecular weight (Mn) [GPC]:1.05

Weight average molecular weight (Mw) as measured by the polystyrene conversion method: 484

Amount of sodium remaining in the resulting product: Not more than 0.01 ppm

Total acid value in the resulting product: Not more than 0.01

Results obtained in evaluating fundamental performance as a lubricating oil and electrical insulating properties of the polycarbonate obtained are shown in Table 4.

EXAMPLE 22

Example 21 was repeated to obtain 736 g of a polycarbonate except that the charged amounts of the neopentyl glycol and the methanol solution of 28% by weight of NaOCH$_3$ were changed to 258 g (2.48 mol) and 2.0 g (NaOCH$_3$ 0.011 mol), respectively, and 2707 g (11.75 mol) of di-[1,3-dimethylbutyl]carbonate was used in place of the di-[2ethylhexyl]carbonate, and that the reaction was carried out under reduced pressure of 50–20 mm Hg and at a reaction temperature of 120°–135° C.

The amount of the distilled 1,3-dimethylbutanol was 502 g (4.91 mol) and the yield of said 1,3-dimethylbutanol was 99%.

The polycarbonate thus obtained was a liquid, and from the result of $^1$H-NMR, IR and GC-Ms analysis, it was found that said polycarbonate has a structure represented by the following formula.

$(CH_3)_2C[CH_2OCOOCH(CH_3)CH_2CH(CH_3)_2]_2$

The polycarbonate obtained was analyzed by means of $^1$H-NMR, whereby such peaks as mentioned below appeared in the chart. In this case, CDCl$_3$ was used as the solvent therefor.

0.93 ppm (d 12H), 1.02 ppm (s 6H), 1.27 ppm (d 6H), 1.31 ppm (2H), 1.62 ppm (2H), 1.70 ppm (2H), 3.97 ppm (s 4H), 4.85 ppm (2H)

On GC-Ms analysis of this polycarbonate, a molecular ion peak of M$^+$ appeared at m/e=361 in the chart.

Data on the infrared absorption spectrum of the polycarbonate obtained are shown below, in which main peaks are as follows:

νC-H 2800–3000 cm$^{-1}$

δC-H 1460–1480 cm$^{-1}$

νV=O 1745 cm$^{-1}$, 1250 cm$^{-1}$

Further, the results of GPC analysis of the polycarbonate are shown below. In that case, it was confirmed that a condensate of neopentyl-di-[1,3-dimethylbutyl]carbonate partly exists in the resulting product.

Weight average molecular weight (Mw)/number average molecular weight (Mn) [GPC] : 1.09

Weight average molecular weight (Mw) as measured by the polystyrene conversion method: 440

Amount of sodium remaining in the resulting product: Not more than 0.01 ppm

Total acid value in the resulting product: Not more than 0.01

Results obtained in the evaluation of the polycarbonate thus obtained on fundamental performance as a lubricating oil and electrical insulating properties are shown in Table 4.

EXAMPLE 23

Example 22 was repeated to obtain 420 g of a polycarbonate except that the charged amounts of the neopentyl glycol, methanol solution of 28% by weight of NaOCH$_3$ and di-[1,3-dimethylbutyl]carbonate were changed to g (1.22 mol), 0.68 g (NaOCH$_3$ 0.003 mol) and 2817 g (12.23 mol), respectively, and that the reaction was carried out under the same conditions as in Example 21.

The amount of the distilled 1,3-dimethylbutanol was 245 g (2.40 mol) and the yield of said 1,3-dimethylbutanol was 98%.

The polycarbonate thus obtained was a liquid, and the results of $^1$H-NMR, IR and GC-Ms analysis thereof were the same as in Example 22, and the structure thereof was the same as in the polycarbonate of Example 22.

Further, GPC analytical results of the polycarbonate obtained are shown below. In this case, it was confirmed that a condensate of neopentyl-di-[1,3-dimethylbutyl]carbonate partly exists in the resulting product.

Weight average molecular weight (Mw)/number average molecular weight (Mn) [GPC]: 1.09

Weight average molecular weight (Mw) as measured by the polystyrene conversion method: 372

Amount of sodium remaining in the resulting product: Not more than 0.01 ppm

Total acid value in the resulting product: Not more than 0.01

Results obtained in the evaluation of the polycarbonate thus obtained on fundamental performance as a lubricating oil and electrical insulating properties are shown in Table 4.

EXAMPLE 24

The same reactor as used in Example 21 was charged with g (3.01 mol) of neopentyl glycol, 2735 g (21.00 mol) of 2-ethylhexanol, 1901 g (21.13 mol) of dimethyl carbonate and 1.3 g (NaOCH$_3$ 0.0067 mol) of methanol solution of 28% by weight of NaOCH$_3$.

The mixture thus charged in the reactor was heated for 11 hours at atmospheric pressure and 110°–160° C. and the resulting methanol was distilled off. The amount of the distilled methanol was 852 g (26.62 mol), and the yield of said methanol was 98.5%.

Subsequently, the mixture was allowed to undergo reaction for 8 hours at 130°–170° C. under reduced pressure (130–10 mm Hg), while distilling off methanol, dimethyl carbonate, 2-ethylhexanol and methyl-2-ethylhexyl carbonate.

The reaction mixture thus obtained was post-treated in the same manner as in Example 21 to obtain 1103 g of a polycarbonate.

The polycarbonate thus obtained was a liquid, and it was then confirmed that the analytical results of $^1$H-NMR, IR and GC-Ms analysis obtained on this polycarbonate .agree with those obtained in Example 21 and said polycarbonate has the same structure as in the polycarbonate of Example 21.

Further, GPC analytical results of the polycarbonate thus obtained are shown below. In this case, it was confirmed that a condensate of neopentyl-di-[2-ethylhexyl]carbonate partly exists in the resulting product.

Weight average molecular weight (Mw)/number average molecular weight (Mn) [GPC]: 1.06

Weight average molecular weight (Mw) as measured by the polystyrene conversion method: 500

Amount of sodium remaining in the resulting product: Not more than 0.01 ppm

Total acid value in the resulting product: Not more than 0.01

Results obtained in the evaluation of the polycarbonate thus obtained on fundamental performance as a lubricating oil and electrical insulating properties are shown in Table 4.

EXAMPLE 25

The same reactor as used in Example 21 was charged with 136 g (1.00 mol) of pentaerythritol, 1481 g (20.01 mol) of n-butanol, 1801 g (20.02 mol) of dimethyl carbonate and 0.94 g (NaOCH$_3$ 0.0048 mol) of a methanol solution of 38% by weight of NaOCH$_3$.

The mixture thus charged in the reactor was heated for 7 hours at atmospheric pressure and 90°–135° C., and the resulting methanol was distilled off. The amount of the distilled methanol was 760 g (23.76 mol), and the yield of the methanol was 99.0%.

Subsequently, the mixture was allowed to undergo reaction for 10 hours at 140–150° C. under reduced pressure (760–110 nun Hg), while distilling off methanol, dimethyl carbonate, n-butanol and methylbutyl carbonate.

The reaction mixture thus obtained was post-treated in the same manner as in Example 21 to obtain 407 g of a polycarbonate.

The polycarbonate thus obtained was a viscous liquid; and from the results of $^1$H-NMR, IR and GPC analysis, it was found that the polycarbonate has such a structure as represented by the following formula.

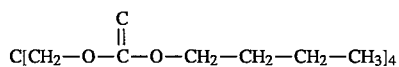

The polycarbonate obtained was analyzed by means of $^1$H-NMR, whereby such peaks as mentioned below appeared in the chart. In this case, CDCl$_3$ was used as the solvent therefor.

0.95 ppm (tri 12H), 1.42 ppm (8}t), 1.65 ppm (8H), 4.14 ppm (tri 8H), 4.24 ppm (s 8H)

Figure 4:
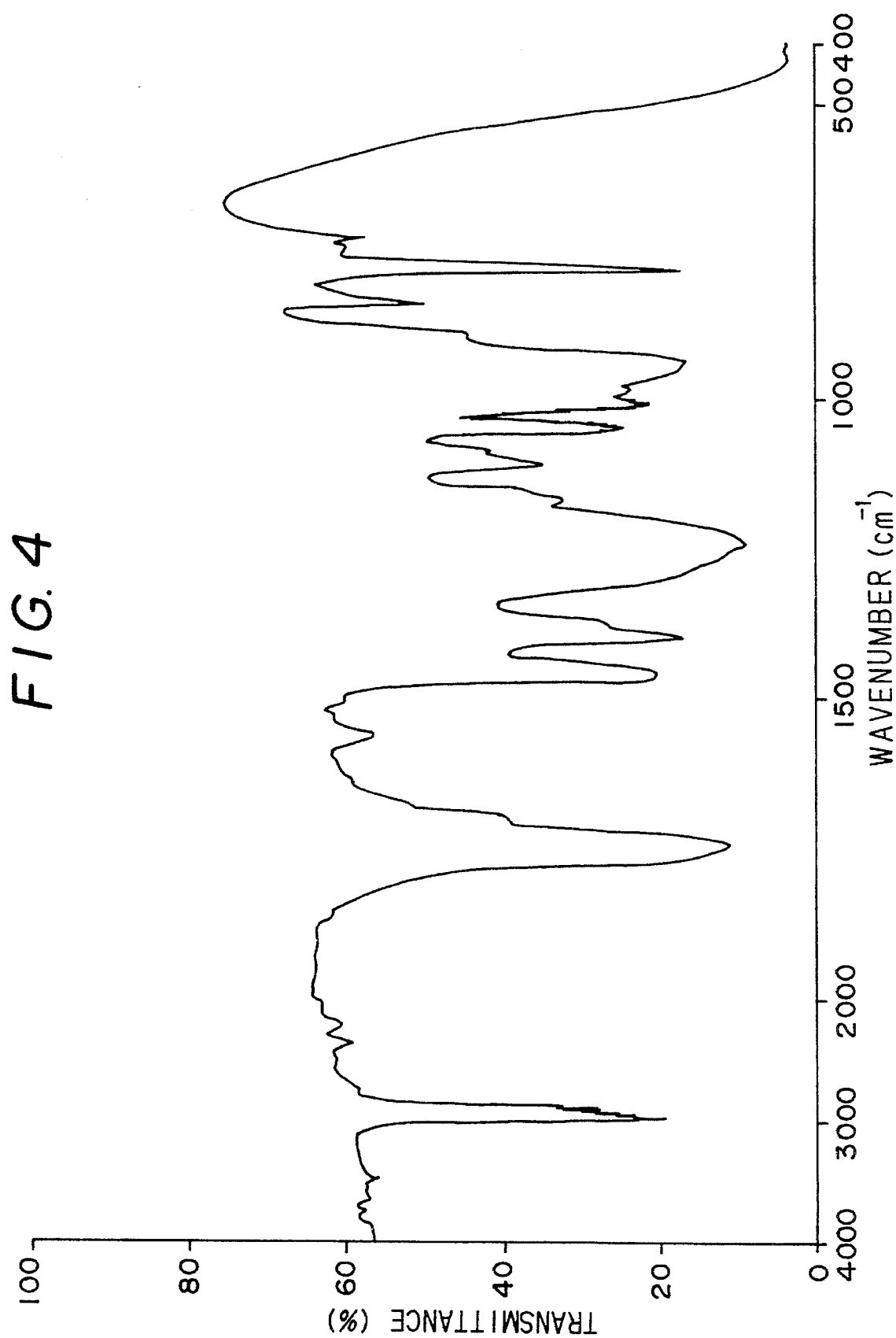

The infrared absorption spectrum of the polycarbonate obtained are shown in FIG. 4.

Further, GPC analytical results of the polycarbonate obtained are shown below. In this case, it was confirmed that a condensate of the polycarbonate represented by the above-mentioned formula partly exists in the resulting product.

Weight average molecular weight (Mw)/number average molecular weight (Mn) [GPC]: 1.19

Weight average molecular weight (Mw) as measured by the polystyrene conversion method: 766

Amount of sodium remaining in the resulting product: Not more than 0.01 ppm

Total acid value in the resulting product: Not more than 0.01

Results obtained in the evaluation of the polycarbonate obtained on fundamental performance as a lubricating oil and electrical insulating properties are shown in Table 4.

TABLE 4

|  | Example 21 | Example 22 | Example 23 | Example 24 | Example 25 |
|---|---|---|---|---|---|
| Viscosity characteristics |  |  |  |  |  |
| 40° C. kinematic viscosity [cSt] | 30.16 | 29.94 | 13.78 | 34.03 | 611.8 |
| 100° C. kinematic viscosity [cSt] | 4.51 | 4.04 | 2.67 | 4.92 | 29.7 |
| Pour point [°C.] | −45 | −40 | −40 | −45 | −15 |
| Electrical insulating properties Volume resistivity [Ω · cm] | $1.1 \times 10^{14}$ | $1.0 \times 10^{14}$ | $6.8 \times 10^{14}$ | $1.7 \times 10^{14}$ | $1.0 \times 10^{13}$ |
| Load bearing capacity [lbf] | 810 | 750 | 620 | 780 | 1050 |
| Compatibility with Freon R-134a |  |  |  |  |  |
| (1) (Note 1) | o | o | o | o | o |
| (2) Critical temperature [°C.] (Note 2) |  |  |  |  |  |
| High temperature side | >+100 | >+100 | >+100 | >+100 | +63 |
| Low temperature side | −27 | −65 | <−65 | −23 | −22 |

(Note 1)
o: Compatible
x: Not compatible
(Note 2)
Lubricating oil: 15% by weight
Freon R-134a: 85% by weight The polycarbonates obtained in Examples 21–25 were all found to be excellent in lubricating properties and electrical insulating properties obtained from load bearing capacities of these polycarbonates.

EXAMPLE 31

A 5-liter flask equipped with a distillation column of 1 sieve tray was charged with 341 g (2.89 mol) of 3-methylpentane diol, 3,873 g (15.01 mol) of di[methylhexyl]carbonate and 1.0 g (NaOCH$_3$ 0.005 mol) of a methanol solution of 28% by weight of NaOCH$_3$.

The mixture charged in the flask was allowed to undergo reaction for 10 hours at 130°–160° C. under reduced pressure (40–10 mm Hg) while distilling off the resulting methylhexanol. The amount of the distilled methylhexanol was 661 g (5.70 mol), and the yield of the methylhexanol was 99%.

The reaction mixture thus obtained was charged with an aqueous solution containing ammonium carbonate in an amount of five times the molar quantity of NaOCH$_3$ used, thereby neutralizing the catalyst present therein. The reaction mixture thus treated was washed with water, and unaltered di[methylhexyl]carbonate was then removed therefrom to obtain 902 g of a polycarbonate.

The polycarbonate thus obtained was a liquid, and from the results of $^1$H-NMR, IR and GC-Ms analysis, it was found that the polycarbonate has such a structure as mentioned below.

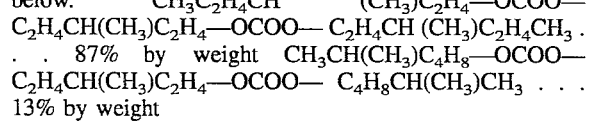

87% by weight CH$_3$CH(CH$_3$)C$_4$H$_8$—OCOO— C$_2$H$_4$CH(CH$_3$)C$_2$H$_4$—OCOO— C$_4$H$_8$CH(CH$_3$)CH$_3$ . . . 13% by weight The polycarbonate obtained was analyzed by means of $^1$H-NMR, whereby such peaks as mentioned below appeared in the chart. In this case, CDCl$_3$ was used as the solvent therefor.

0.85–0.9 ppm (6H), 0.9–1.0 ppm (3H), 1.2–1.45 ppm (8H), 1.45–1.6 ppm (17H), 1.6–1.7 ppm (17H), 1.7–1.9 ppm (17H), 4.1–4.2 ppm (8H)

On GC-Ms analysis of this polycarbonate, a molecular ion of M$^+$ appeared at m/e=403 in the chart.

Figure 5:
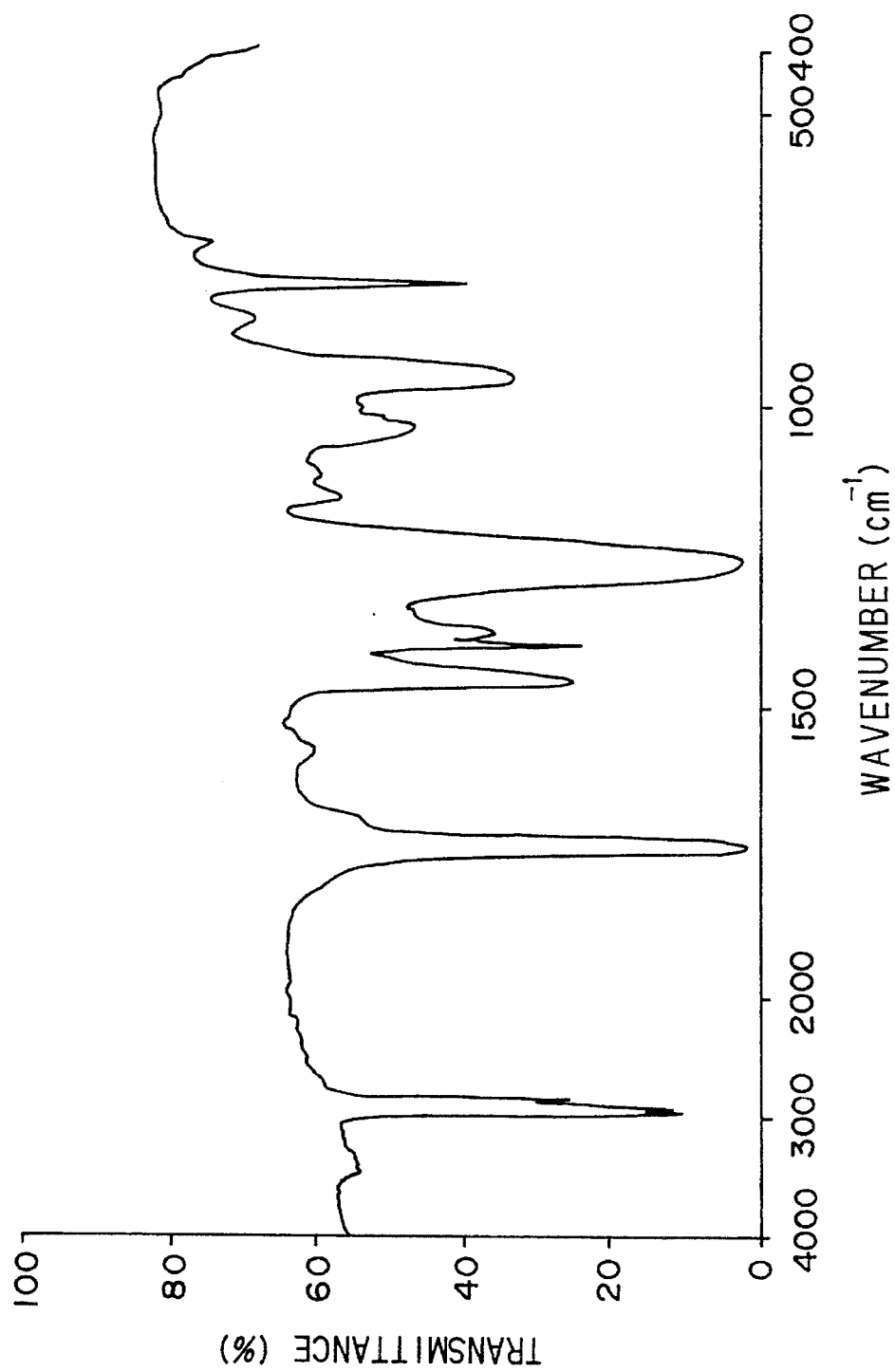
FIG. 5 is a graph showing IR absorption spectra of polycarbonates obtained in Examples 31 and 32, respectively.

The infrared absorption spectrum of the polycarbonate obtained are shown in FIG. 5.

Further, the results of GPC analysis of the polycarbonate obtained are shown below. In that case, it was confirmed that a condensate of 3-methylamylene-dimethylhexyl]carbonate partly exists in the resulting product.

Weight average molecular weight (Mw)/number average molecular weight (Mn) [GPC]: 1.05

Weight average molecular weight (Mw) as measured by the polystyrene conversion method: 670

Amount of sodium remaining in the resulting product: Not more than 0.01 ppm

Total acid value in the resulting product: Not more than 0.01

Results obtained in the evaluation of the thus obtained polycarbonate on fundamental performance as a lubricating oil and electrical insulating properties are shown in Table 5.

EXAMPLE 32

The same flask as used in Example 31 was charged with 496 g (4.2.0 mol) of 3-methylpentane diol, 2457 g (21.1 mol) of methylhexanol (a mixture of 87 moles of 3-methylhexanol and 13 moles of 5-methylhexanol), 1899 g (21.1 mol) of dimethylcarbonate and 1.9g (NaOCH$_3$ 0.0007 mol) of a methanol solution of 28% by weight of NaOCH$_3$.

The mixture charged in the flask was heated for 11 hours at 110°–160° C. and atmospheric pressure to distilling off the resulting methanol. The yield of methanol was 98.0%.

Subsequently, this mixture was allowed to undergo reaction for 8 hours at 130°–170° C. under reduced pressure, while distilling off methanol, dimethyl carbonate, methylhexanol and methyl-methylhexyl carbonate.

The reaction mixture thus obtained was post-treated in the same manner as in Example 31 to obtain 1,300 g of a polycarbonate.

The polycarbonate thus obtained was a liquid, and it was confirmed that the analytical results of the polycarbonate by $^1$H-NMR, IR and GC-Ms coincide with those obtained in Example and said polycarbonate has the same structure as that of the polycarbonate of Example 31. Further, the results of GPC analysis of the polycarbonate obtained are shown below. In that case, it was confirmed that a condensate of 3-methylamyl-di-methylhexyl carbonate partly exists in the resulting product.

Weight average molecular weight (Mw)/number average molecular weight (Mn) [GPC]: 1.06

Weight average molecular weight (Mw) as measured by the polystyrene conversion method: 731

Amount of sodium remaining in the resulting product: Not more than 0.01 ppm

Total acid value in the resulting product: Not more than 0.01

Results obtained in the evaluation of the thus obtained polycarbonate on fundamental performance as a lubricating oil and electrical insulating properties are shown in Table 5.

TABLE 5

|  | Example 31 | Example 32 |
|---|---|---|
| Viscosity Characteristics |  |  |
| 100° C. kinematic viscosity [cSt] | 4.8 | 4.9 |
| 40° C. kinematic viscosity [cSt] | 25.0 | 24.1 |
| Viscosity index | 126 | 126 |
| Pour point [°C.] | −60 | −60 |
| Electrical insulating properties Volume resistivity ($\psi \cdot$ cm] | $1.1 \times 10^{15}$ | $2.0 \times 10^{15}$ |
| Load bearing capacity [lbf] | 910 | 950 |
| Compatibility with Freon R-134a (Note 1) | o | o |
| Critical Temperature [°C.] (Note 2) |  |  |
| High temp. side | >+95 | >+94 |
| Low temp. side | −42 | −46 |

(Note 1)
o: Compatible
x: Not Compatible
(Note 2)
Lubricating oil: 15% by weight
Freon R-134a: 85% by weight

EXAMPLE 41

A 3-liter flask equipped with a distillation column (10 sieve trays) was charged with 192 g (1.00 mol) of tripropylene glycol, 1301 g (9.99 mol) of 2-ethylhexanol, 901 g (10.01 mol) of dimethyl carbonate and a methanol solution of 28% by weight of $NaOCH_3$ ($NaOCH_3$ 0.001 mol).

The mixture in the flask was heated for 12 hours at 96°–175° C. and atmospheric pressure to distill off the resulting methanol. The amount of the distilled alcohol was 365 g (11.41 mol).

Subsequently, the pressure of the system was gradually reduced, and the reaction was carried out for 5 hours at 170°– 190° C. under a pressure of from 760 mm Hg to 10 mm Hg to distill off 17 g of methanol, 139 g of dimethyl carbonate, 6 g of 2-ethylhexanol and 44 g of methyl-2-ethylhexyl carbonate.

The distilled methanol was 99.8% of the theoretical amount. The catalyst remained in 160Q g (recovery 99.7%) of the thus obtained reaction mixture was neutralized by the addition thereto of an aqueous solution containing ammonium carbonate 5 times the molar quantity of $NaOCH_3$ used, and the mixture was then washed 3 times with water to separate an aqueous phase therefrom. Subsequently, an oily phase was distilled under reduced pressure to remove unaltered di-[2-ethylhexyl]carbonate therefrom, whereby 446 g of a carbonate reaction product was obtained.

The yield of carbonate product thus obtained was 89%.

This product had a kinematic viscosity (100° C., JIS K-2283) of 5.1 cSt. The amount of sodium remaining in the resulting carbonate was not more than 0.01 ppm, and the total acid value was not more than 0.01.

On NMR analysis, it was confirmed that the main product is tripropylene glycol di-[2-ethylhexyl]carbonate.

EXAMPLE 42–43

Example 41 was repeated to obtain a carbonate product except that the amounts of the tripropylene glycol, 2-ethylhexanol, dimethyl carbonate and methanol solution of 28% by weight of $NaOCH_3$ used were changed respectively to those Indicated in Table 6.

Results obtained are shown in Table 6.

EXAMPLE 44–50

Example 41 was repeated to obtain a carbonate product except that the kind and amount of the polyol [$R_{22}(OH)_l$] and monoalcohol $R_{23}OH$ fed had been changed to those indicated in Table 6.

Results obtained are shown in Table 6.

TABLE 6

|  | Kinds of starting materials and amounts thereof |  |  |  | $CH_3OH$ produced |  | Carbonate produced |  | Kinematic viscosity of carbonate |
|---|---|---|---|---|---|---|---|---|---|
|  | $R_{22}(OH)_l$ | $R_{23}OH$ | $CH_3OCO_2CH_3$ | $NaOCH_3$ |  | Yield |  | Yield | (100° C.) |
|  | [mol] | [mol] | [mol] | [mol] | [g] | [%] | [g] | [%] | [cSt] |
| Ex. 42 | TPG 3.30 | 2-EHOH 16.50 | 16.51 | 0.0036 | 731 | 98.9 | 1365 | 82.1 | 5.7 |
| Ex. 43 | TPG 2.40 | 2-EHOH 7.20 | 14.40 | 0.0026 | 385 | 100 | 925 | 76.4 | 7.8 |
| Ex. 44 | TPG 1.41 | MIBC 25.45 | 16.92 | 0.0207 | 892 | 98.6 | 567 | 89.9 | 4.3 |
| Ex. 45 | NPG 3.01 | 2-EHOH 21.00 | 21.13 | 0.0067 | 851 | 98.6 | 1103 | 88.3 | 4.9 |
| Ex. 46 | NPG 2.71 | 2-EHOH 13.51 | 13.51 | 0.0048 | 592 | 97.7 | 973 | 86.0 | 5.8 |
| Ex. 47 | NPG 4.01 | n-$C_7H_{15}OH$ 20.01 | 20.07 | 0.0052 | 871 | 97.2 | 1235 | 68.2 | 4.4 |
| Ex. 48 | PE 1.00 | n-$C_4H_9OH$ 20.01 | 20.01 | 0.0048 | 760 | 98.9 | 407 | 75.9 | 27.8 |

TABLE 6-continued

| | Kinds of starting materials and amounts thereof | | | | | | CH$_3$OH produced | | Carbonate produced | | Kinematic viscosity of carbonate |
|---|---|---|---|---|---|---|---|---|---|---|---|
| | R$_{22}$(OH)$_l$ | | R$_{23}$OH | | CH$_3$OCO$_2$CH$_3$ | NaOCH$_3$ | | Yield | | Yield | (100° C.) |
| | | [mol] | | [mol] | [mol] | [mol] | [g] | [%] | [g] | [%] | [cSt] |
| Ex. 49 | DPG | 2.00 | 2-EHOH | 10.07 | 10.07 | 0.0041 | 437 | 97.1 | 655 | 73.4 | 5.0 |
| Ex. 50 | SU-460 | 1.42 | n-C$_4$H$_9$OH | 42.63 | 42.63 | 0.0052 | 1622 | 99.1 | 1726 | 79.3 | 32.1 |

[Notes]
TPG: Tripropylene glycol, NPG: Neopentyl glycol, PE: Pentaerysthritol
DPG: Dipropylene glycol, SU-460: Propylene oxide adduct of sucrose (SU-460 of PPG-polyfunctional Series), a product of Mitsui Toatsu Chem. Inc.
2-EHOH: 2-Ethylhexanol, MIBC: Methylisobutylcarbinol A 3-liter reactor equipped with a 10 sieve tray distillation column was charged with a mixture containing 802 g (2.00 mol) of polypropylene having an average molecular weight of 400, 1,804 g (20.03 mol) of dimethyl carbonate and 0.39 g (NaOCH$_3$: 0.0020 mol) of a methanol solution of 28% by weight of NaOCH$_3$.

The mixture was heated at 110°–120° C. and ordinary pressure to carry out the reaction while distilling off the resulting methanol as the dimethyl carbonate azeotrope, whereby the methanol ceased to distill after 8 hours. The methanol thus formed was 127 g (3.97 mol), and the yield of methanol was 99%.

The reaction mixture thus obtained had the Na content of 44 ppm.

The reaction mixture was then charged with hexane and an aqueous solution obtained by dissolving 0.96 g (0.01 mol) of ammonium carbonate in 1 liter of distilled water, stirred thoroughly to neutralize the catalyst, and left at rest followed by separation of an aqueous phase.

Subsequently, an oily phase remained was washed three times with 1 liter of distilled water, and the hexane and unaltered dimethyl carbonate were removed from the oily phase containing the same to obtain 1,032 g of a polycarbonate.

The electrical insulation properties of this polycarbonate as measured in terms of a volume resistivity which is regarded as a measure of said properties was $7.0 \times 10^{11}$ Ω.cm.

This polycarbonate charged with 1 liter of toluene and 20 g of an inorganic ion exchanger (Grade IXE-600, a product of Toa Gosei Chemical Industry Co., Ltd.) was allowed to undergo ion exchange by heating with stirring at 100° C. for 3 hours. Subsequently, the resulting liquid thus treated was cooled and filtered to remove the toluene therefrom, whereby 1,011 g of a purified polycarbonate.

Shown in Table 7 are the results of analysis of inorganic elements and free ions contained in the purified polycarbonate thus obtained.

This polycarbonate was found to have a volume resistivity of $4.2 \times 10^{12}$ Ω.cm, and it was understood that the polycarbonate has improved in electrical insulation properties by virtue of the above-mentioned treatment with inorganic ion exchanger.

The polycarbonate obtained was a viscous liquid which, on analysis by means of proton NMR and GPC, comprises polypropylene glycol dimethyl carbonate as a main constituent. The weight average molecular weight/number average molecular weight (Mw/Mn) ratio as measured by means of GPC in the polyolefin was 1.1.

TABLE 7

| | Element | | | | Free ion | | | | |
|---|---|---|---|---|---|---|---|---|---|
| Treatment method | Na | Fe | Cl | S | Cl$^-$ | NO$_3^-$ | PO$_3^{3+}$ | SO$_4^{-2}$ | HCOO$^-$ |
| Water-washing | 0.036 | Not more than 0.01 | Not more than 0.1 | Not more than 1.0 | Not more than 0.5 | Not more than 1.0 | Not more than 1.0 | Not more than 1.0 | Not more than 1.0 |
| Water-washing and ion exchange treatment with inorganic ion exchanger | Not more than 0.01 | Not more than 0.01 | Not more than 0.1 | Not more than 1.0 | Not more than 0.5 | Not more than 1.0 | Not more than 1.0 | Not more than 1.0 | Not more than 1.0 |

Unit: ppm

Shown in Table 7 are the results of analysis of inorganic elements and free ions contained in the polycarbonate thus obtained.

By virtue of the water-washing treatment mentioned above, the Na content in the polycarbonate reduced up to 0.036 ppm, and other elements and free ions were all below the limit of detection.

EXAMPLE 62

Example 61 was repeated except that in place of the polypropylene glycol and dimethyl carbonate there were used 106 g (0.55 mol) of tripropylene glycol and 1,575 g (5.51 mol) of di-[2-ethylhexyl]carbonate, respectively, and the amount of the methanol solution of 28% by weight of NaOCH$_3$ used was changed to 0.11 g (NaOCH$_3$ 0.0006 mol).

The reaction gave 2-ethylhexanol in an amount of 143 g and in 100% yield.

The reaction mixture thus obtained contained 10.1 ppm of sodium.

This reaction mixture was subjected, in the same manner as in Example 61, to neutralization, water-washing and removal by distillation of unaltered di[ethylhexyl]carbonate, whereby 244 g of a polycarbonate was obtained.

Shown in Table 8 are the results of analysis of inorganic elements and free ions contained in the polycarbonate thus obtained.

The electrical insulation properties of this polycarbonate as measured in terms of a volume resistivity which is regarded as a measure of said properties was $2.8 \times 10^{12}$ Ω.cm.

This polycarbonate was subjected, in the same manner as in Example 61, to treatment with an inorganic exchanger (Grade IXE-600, a product of Toa Gosei Chemical Industry Co., Ltd.), whereby 239 g of a purified polycarbonate was obtained.

Shown in Table 8 are the results of analysis of inorganic elements and free ions contained in the purified polycarbonate.

This purified polycarbonate was found to have a volume resistivity of $2.1 \times 10^{13}$ Ω.cm, and it was understood that the polycarbonate has improved apparently in electrical insulation properties by virtue of the above-mentioned treatment with inorganic ion exchanger.

The polycarbonate obtained was a viscous liquid which, on analysis by means of proton NMR and GPC, comprises polytripropylene glycol-di-[2-ethylhexyl]carbonate as a main constituent. The weight average molecular weight/ number average molecular weight (Mw/Mn) ratio as measured by means of PGC in the polyolefin was 1.05.

Water was added to the resulting mixture to remove the catalyst and, from the resulting mixture, DMDPC was distilled off to obtain 770g of polycarbonate represented by the following formula:

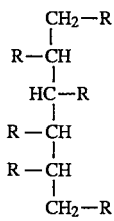

wherein R is $-(OC_3H_6))_2OCOO(C_3H_6O)_2CH_3$.

The resulting polycarbonate was analyzed by GPC analysis and it was confirmed that the polycarbonate is composed of 64.4% of monomer and 35.6% of polymer, and polycarbonate condensate partially existed, and the results are shown in Table 9.

Results of evaluation of fundamental performance as lubricating oil are shown in Table 10.

(Preparation of Monocarbonate)

A 3-liter flask equipped with a distillation column of a 10-sieve tray was charged with 1,134g of polypropylene glycol monomethyl ether (MPG) having an average molecular weight (Mn) of 1.000, 215g of dimethylcarbonate (DMC) and 6.0g of a methanol solution of 28% by weight of $NaOCH_3$.

TABLE 8

| Treatment method | Element | | Free ion | | | | |
|---|---|---|---|---|---|---|---|
| | Na | Cl | Cl⁻ | $NO_3^{31}$ | $PO_3^{3+}$ | $SO_4^{-2}$ | HCOO⁻ |
| Water-washing | 0.66 | Not more than 0.1 | Not more than 0.5 | Not more than 1.0 | Not more than 1.0 | Not more than 1.0 | Not more than 1.0 |
| Water-washing and ion exchange treatment with inorganic ion exchanger | Not more than 0.01 | Not more than 0.1 | Not more than 0.5 | Not more than 1.0 | Not more than 1.0 | Not more than 1.0 | Not more than 1.0 |

Unit: ppm

EXAMPLE 63

(Preparation of Polycarbonate)

A 5-liter flask equipped with a distillation column was charged with 389g of a propylene oxide adduct of sorbitol having an average molecular weight (Mn) of 900 (SP-12P: product of Toho Kegaku K.K.), 3,484g of $CH_3O(C_3H_6O)_2COO(C_3H_6O)_2CH_3$ (dimethoxydipropoxy carbonate: DMDPC) and 4.2 g of methanol solution containing 28% by weight of $NaOCH_3$.

The mixture was allowed to react by heating at 140°–175° C. at reduced pressure (30–5 mmHg) for 3.5 hours while distilling off the resulting methylpropylene diglycol, whereby 382 g of methylpropylene diglycol was distilled off (reaction yield: 99.4%).

The resulting mixture was allowed to react by heating at 103°–175° C. at normal pressure for 2.5 hours and then at 160°–170° C. at a reduced pressure (760–10 mmHg) for 3.0 hours, whereby 192 g of a distilled liquid was distilled off the distilled liquid contained 36.2 g of methanol (reaction yield: 99.7%).

Water and hexane were added to the resulting mixture to remove the catalyst and, from the resulting mixture, low boiling point substances were distilled off to obtain 1,140 g of monocarbonate represented by the following formula: $CH_3O(C_3H_6O)_nCOO(C_3H_6O)_nCH_3$ (wherein average n value is 17).

The resulting monocarbonate was analyzed by GPC analysis and it was confirmed that the monocarbonate is composed of 100% of monomer and has 2,058 of an average molecular weight (Mn), and the results are shown in Table 9.

Results of evaluation of fundamental performance as lubricating oil are shown in Table 10.

(Preparation of Lubricating Oil)

The polycarbonate and the monocarbonate thus obtained were mixed at a ratio (polycarbonate/monocarbonate) of 75/25 to obtain a lubricating oil having 20 cSt of a 100° C. kinematics viscosity and not less than 120 of a viscosity index, not less than 65° C. of a compatibility with Freon-134a and R-12 at high-temperature side and excellent lubricating properties.

The properties of the lubricating oil obtained were shown in Table 11.

EXAMPLE 64

(Preparation of Polycarbonate)

The preparation of the polycarbonate in Example 63 was repeated except that 450 g of a propylene oxide adduct of sorbitol (SP-18P: a product of Toho Kagaku K. K.) in place of the propylene oxide adduct of sorbitol (SP-12P) and 3,645g of the $CH_3O(C_3H_6O)_3COO(C_3H_6O)CH_3$ (dimethoxydipropoxy carbonate: DMDPC) were used.

In results, there was obtained 765 g of a polycarbonate represented by the following formula:

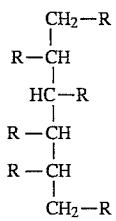

wherein R is $—(OC_3H_6)_3OCOO(C_3H_6O)_2CH_3$.

The resulting polycarbonate was analyzed by GPC analysis and it was confirmed that the polycarbonate is composed of 62.6% of monomer and 37.4% of polymer, and the results are shown in Table 9.

Results of evaluation of fundamental performance as lubricating oil are shown in Table 10.

(Preparation of Monocarbonate)

The same procedure as in the preparation of monocarbonate in Example 63 was repeated to obtain a monocarbonate, and the results are shown in Table 9.

Results of evaluation of fundamental performance as lubricating oil are shown in Table 10.

(Preparation of Lubricant Oil)

The polycarbonate and the monocarbonate thus obtained were mixed at a ratio (polycarbonate/monocarbonate) of 90/10 to obtain a lubricating oil.

The properties of the lubricating oil obtained were shown in Table 11.

EXAMPLE 65

(Preparation of Polycarbonate)

The preparation of polycarbonate in Example 63 was repeated to obtain a polycarbonate, and the results are shown in Table 9.

Results of evaluation of fundamental performance as lubricating oil are shown in Table 10.

(Preparation of Monocarbonate)

A 3-liter flask equipped with a distillation column of a 10-sieve tray was charged with 1,135 g (1.16 mol) of polypropylene glycol monomethyl ether (MPG) (a product of Toho Kagaku Kogyo K. K.) having an average molecualr weight (Mn) of 978, 215 g (2.39 mol) of dimethylcarbonate and 6.2 g ($NaOCH_3$: 0.032 mol) of a methanol solution of 28% by weight of $NaOCH_3$.

The resulting mixture was allowed to react by heating at 100–170 at ordinary pressure for 3.5 hours, while distilling off methanol, whereby 35 g (1.09 mol) of methanol was distilled. The yield of methanol was 94%.

Then the reaction mixture was allowed to react by gradually reducing the pressure in the reaction system (760–5 mmHg) and heating at 165° C. while distilling off methanol formed. In results, the distillation of the methanol stopped after 4 hours. The total amount of the distilled methanol was 37 g(1.16 mol) and the yield of the methanol was 100%. The total amount of the distilled dimethylcarbonate was 160 g (1.78 mol).

Hexane was added to the resulting mixture and then the catalyst was neutralized with an aqueous solution containing ammonium carbonate in an amount of five times the molar quantity of the $NaOCH_3$ used. The reaction mixture thus treated was washed with water, and the hexane and water were removed therefrom to obtain 1,140 g of a carbonate compound.

The monocarbonate compound thus obtained is a viscous liquid not containing polypropylene glycol monomethyl ether and, in the results of GPC analysis, there was observed a single peak for 2,403 of a weight-average molecular weight (Mw), and the results are shown in Table 9. Further, the carbonate compound has a polydisperse ratio (Mw/Mn (number average molecular weight)) of 1.13.

Results of evaluation of fundamental performance as lubricating oil are shown in Table 10.

(Preparation of Lubricant Oil)

the polycarbonate and the monocarbonate thus obtained were mixed at a ratio (polycarbonate/monocarbonate) of 20/80 to obtain a lubricating oil.

The properties of the lubricating oil obtained are shown in Table 11.

TABLE 9

| | | | | | | | | GPC analysis | |
|---|---|---|---|---|---|---|---|---|---|
| | Kinds of starting materials and amounts thereof | | | | | | Yield | monomer | polymer |
| Example 63 polycarbonate | SP-12P | 389 g | DMDPC | 3,484 g | methanol solution of | | 4.2 g | 770 g | 64.4% | 35.6% |

TABLE 9-continued

| | | | | | | | | GPC analysis | |
|---|---|---|---|---|---|---|---|---|---|
| | | Kinds of starting materials and amounts thereof | | | | | Yield | monomer | polymer |
| | monocarbonate | MPG | 1,134 g | DMC | 215 g | 28% NaOCH₃ methanol solution of 28% NaOCH₃ | 6.0 g | 1,140 g | 100% | — |
| Example 64 | polycarbonate | SP-18P | 450 g | DMDPC | 3,645 g | 28% NaOCH₃ methanol solution of 28% NaOCH₃ | 4.2 g | 765 g | 62.6% | 37.4% |
| | monocarbonate | MPG | 1,134 g | DMC | 215 g | 28% NaOCH₃ methanol solution of 28% NaOCH₃ | 6.0 g | 1,140 g | 100% | — |
| Example 65 | polycarbonate | SP-12P | 389 g | DMDPC | 3,484 g | 28% NaOCH₃ methanol solution of 28% NaOCH₃ | 4.2 g | 770 g | 64.4% | 35.6% |
| | monocarbonate | MPG | 1,135 g | DMC | 215 g | 28% NaOCH₃ methanol solution of 28% NaOCH₃ | 6.2 g | 1,140 g | 100% | — |

(Notes)
SP-12P: propylene oxide adduct of sorbitol, a product of Toho Kagaku K.K.;
SP-18P: propylene oxide adduct of sorbitol, a product of Tobo Kagaku K.K.;
DMDPC: dimethyoxydipropoxy carbonate;
MPG: propylene glycol monomethyl ether;
DMC: dimethylcarbonate

TABLE 10

| | Example 63 | | Example 64 | | Example 65 | |
|---|---|---|---|---|---|---|
| | polycarbonate (SP-12P) | monocarbonate (MPG) | polycarbonate (SP-18P) | monocarbonate (MPG) | polycarbonate (SP-12P) | monocarbonate (MPG) |
| Viscosity characteristics | | | | | | |
| 100° C. kinematic viscosity (cSt) | 42.5 | 22.8 | 43.6 | 22.8 | 42.5 | 22.8 |
| viscosity index | 100 | 206 | 121 | 206 | 100 | 206 |
| Load bearing capacity (lbf) | 880 | 820 | 890 | 820 | 880 | 820 |
| Compatibility with Freon R-134a Critical temperature (°C.) (Note 1) | | | | | | |
| High-temperature side | 74 | 51 | 68 | 51 | 74 | 51 |
| Low-temperature side | <−65 | <−65 | <−65 | <−65 | <−65 | <−65 |
| Compatibility with Freon R-12 Critical temperature (°C.) (Note 2) | | | | | | |
| High-temperature side | 65 | 89 | 63 | 89 | 65 | 89 |
| Low-temperature side | <−65 | <−65 | <−65 | <−65 | <−65 | <−65 |

(Note 1) Lubricating oil: 3% by weight and Freon R-134a: 97%
(Note 2) Lubricating oil: 3% by weight and Freon R-12: 97%

TABLE 11

| | Example 63 | | Example 64 | | Example 65 | |
|---|---|---|---|---|---|---|
| | polycarbonate | monocarbonate | polycarbonate | monocarbonate | polycarbonate | monocarbonate |
| Mixing weight ratio | 75 | 25 | 90 | 10 | 20 | 80 |
| Viscosity characteristics | | | | | | |
| 100° C. kinematic viscosity (cSt) | 34.5 | | 39.0 | | 25.5 | |
| viscosity index | 130 | | 131 | | 170 | |
| Load bearing capacity (lbf) | 850 | | 870 | | 830 | |

TABLE 11-continued

|  | Example 63 | | Example 64 | | Example 65 | |
| --- | --- | --- | --- | --- | --- | --- |
|  | polycarbonate | monocarbonate | polycarbonate | monocarbonate | polycarbonate | monocarbonate |
| Compatibility with Freon R-134a Critical temperature (°C.) (Note 1) |  |  |  |  |  |  |
| High-temperature side | 68 |  | 66 |  | 58 |  |
| Low-temperature side | <-65 |  | <-65 |  | <-65 |  |
| Compatibility with Freon R-12 Critical temperature (°C.) (Note 2) |  |  |  |  |  |  |
| High-temperature side | 72 |  | 66 |  | 68 |  |
| Low-temperature side | <-65 |  | <-65 |  | <-65 |  |

(Note 1) Lubricating oil: 3% by weight and Freon R-134a: 97%
(Note 2) Lubricating oil: 3% by weight and Freon R-12: 97%

What is claimed is:

1. A lubricating oil containing;
a polycarbonate represented by the following general formula (II):

$$(R_1O)CH_2(CH(OR_1))_mCH_2(OR_1) \quad (II)$$

wherein $R_1$ is a group represented by the following formula (E) or (F) and m is an integer of 1 to 6;

$$-(C_3H_6O)_nCOOR_2 \quad \ldots (E)$$

wherein $R_2$ is each independently a hydrocarbon group having not more than 30 carbon atoms or a hydrocarbon group containing an ether bond and having 2 to 30 carbon atoms, and n is an integer of 1 to 12, $$-(C_3H_6O)_n(C_2H_4O)_pCOOR_2 \quad \ldots (F)$$

wherein $R_2$ is as defined in the above-mentioned formula (E), and n and p are each an integer of 1 to 12; and
a monocarbonate represented by the following formula (XXX):

$$R_iOCOOR_{ii} \quad \ldots (XXX)$$

wherein each of $R_i$ and $R_{ii}$ is independently a hydrocarbon group having 1–36 carbon atoms, or a glycol ether group represented by the following general formula (XXXI):

$$R_{iii}(OR_{iv}) \quad \ldots (XXXI)$$

wherein $R_{iii}$ is a hydrocarbon group having 1–6 carbon atoms, $R_{iv}$ is ethylene group or propylene group and E is an integer of 1–100.

2. The lubricating oil according to claim 1 wherein in the polycarbonate of general formula (II) at least one of the groups $R_1$ is the group of formula (F) wherein the ratio n/p is from 1/1 to 10/1.

3. The lubricating oil according to claim 1 wherein in the formulas (E) and (F) the groups $R_2$ represent, independently, methyl, ethyl, isopropyl, n-butyl, ethylene glycol monomethyl ether, ethylene glycol monobutyl ether, diethylene glycol monomethyl ether, triethylene glycol monomethyl ether, propylene glycol monomethyl ether, propylene glycol monobutyl ether, dipropylene glycol monoethyl ether or tripropylene glycol mono-n-butyl ether.

4. The lubricating oil of claim 1 wherein the polycarbonate of formula (II) is a polycarbonate of formula (1) or (2) below:

wherein in formula (1) R=—$(CH_2CH(CH_3)O)_nCOOCH_3$ or —$(CH_2CH(CH_3)O)_n(C_2H_4O)COOCH_3$; and in formula (2) R=$(CH_2CH(CH_3)O)_nCOOCH(CH_3)_2$ or —$(CH_2CH(CH_3)O)_n$ $(C_2H_4O)COOCH(CH)_2$, wherein n=1–3.

5. The lubricating oil of claim 1 wherein the monocarbonate of formula (III) is selected from the group consisting of:

$CH_3O(C_3H6O)_n(C_2H_4O)_{m-1}C_2H_4OCOO(C_3H_6O)_n$—$(C_2H_4O)_mCH_3$, $C_2H_5O(C_3H_6O)_n(C_2H_4O)_{m-1}C_2H_4OCOO(C_3H_6O)_n$— $(C_2H4O)_mC_2H_5$,
$C_3H_7O(C_3H_6O)_n(C_2H_4O)_{m-1}C_2H_4OCOO(C_3H_6O)_n$— $(C_2H_4O)_mC_3H_7$,
$C_4H_9O(C_3H_6)_n(C_2H_4O)_{m-1}C_2H_4OCOO(C_3H_6O)_n$— $(C_2H_4O)_mC_4H_9$,
$CH_3OCOO(C_3H_6O)_n(C_2H_4O)_mCH_3$,
$C_3H_7OCOO(C_3H_6O)_n(C_2H_4O)_mCH_3$,
$CH_3OCOO(C_3H_6O)_n(C_2H_4O)_mC_3H_7$, and
$C_2H_5OCOO(C_3H_6O)_n(C_2H_4O)_mC_2H_5$ wherein each of n and m represents an integer of 0–100 with the proviso that n+m=1 to 100.

6. The lubricating oil of claim 1 wherein the mixing weight ratio between the polycarbonate of formula (II) and the monocarbonate of formula (XXX) is in the range of from 75/25 to 20/80.

7. A lubricating oil useful for refrigerator comprising;

a polycarbonate represented by the following general formula (II):

$$(R_1O)CH_2(CH(OR_1))_mCH_2(OR_1) \quad \ldots (II)$$

wherein $R_1$ is a group represented by the following formula (E) or (F) and m is an integer of 1 to 6;

$$-(C_3H_4O)_nCOOR_2 \quad \ldots (E)$$

wherein $R_2$ is each independently a hydrocarbon group having not more than 30 carbon atoms or a hydrocarbon group containing an ether bond and having 2 to 30 carbon atoms, and n is an integer of 1 to 12, $$-(C_3H_6O)_n(C_2H_4O)_pCOOR_2 \quad \ldots (F)$$

wherein $R_2$ is as defined in the above-mentioned formula (E), and n and p are each an integer of 1 to 12; and a monocarbonate represented by the following formula (XXX):

$$R_iOCOOR_{ii} \quad \ldots (XXX)$$

wherein each of $R_i$ and $R_{ii}$ is independently a hydrocarbon group having 1–36 carbon atoms, or a glycol ether group represented by the following general formula (XXXI):

$$R_{iii}(OR_{iv})_l- \quad \ldots (XXXI)$$

wherein $R_{iii}$ is a hydrocarbon group having 1–6 carbon atoms, $R_{iv}$ is ethylene group or propylene group and l is an integer of 1–100; and an ozone layer nondestructive refrigerant.

8. The lubricating oil according to claim 7 wherein in the polycarbonate of general formula (II) at least one of the groups $R_1$ is the group of formula (F) wherein the ratio n/p is from 1/1 to 10/1.

9. The lubricating oil according to claim 7 wherein in the formulas (E) and (F) the groups $R_2$ represent, independently, methyl, ethyl, isopropyl, n-butyl, ethylene glycol monomethyl ether, ethylene glycol monobutyl ether, diethylene glycol monomethyl ether, triethylene glycol monomethyl ether, propylene glycol monomethyl ether, propylene glycol monobutyl ether, dipropylene glycol monoethyl ether or tripropylene glycol mono-n-butyl ether.

10. The lubricating oil of claim 7 wherein the polycarbonate of formula (II) is a polycarbonate of formula (1) or (2) below:

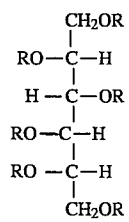

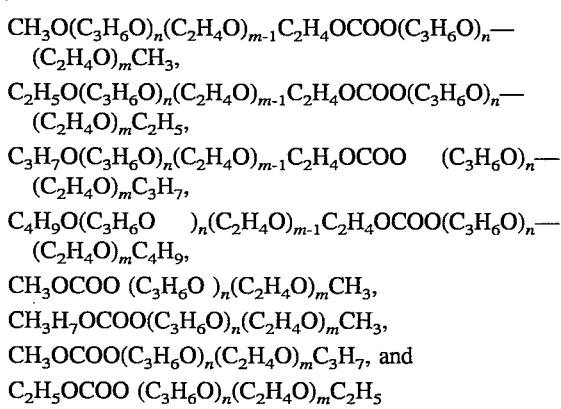

wherein in formula (1) $R=-(CH_2CH(CH_3)O)_nCOOCH_3$ or $-(CH_2CH(CH_3)O)_n(C_2H_4O)COOCH_3$; and in formula (2) $R=(CH_2CH(CH_3)O)_nCOOCH(CH_3)_2$ or $-(CH_2CH(CH_3)O)_n(C_2H_4O)COOCH(CH_3)_2$, wherein $n=1-3$.

11. The lubricating oil of claim 7 wherein the monocarbonate of formula (III) is selected from the group consisting of:

$CH_3O(C_3H_6O)_n(C_2H_4O)_{m-1}C_2H_4OCOO(C_3H_6O)_n-(C_2H_4O)_mCH_3$, $C_2H_5O(C_3H_6O)_n(C_2H_4O)_{m-1}C_2H_4OCOO(C_3H_6O)_n-(C_2H_4O)_mC_2H_5$, $C_3H_7O(C_3H_6O)_n(C_2H_4O)_{m-1}C_2H_4OCOO \quad (C_3H_6O)_n-(C_2H_4O)_mC_3H_7$, $C_4H_9O(C_3H_6O\quad)_n(C_2H_4O)_{m-1}C_2H_4OCOO(C_3H_6O)_n-(C_2H_4O)_mC_4H_9$, $CH_3OCOO\ (C_3H_6O\ )_n(C_2H_4O)_mCH_3$, $CH_3H_7OCOO(C_3H_6O)_n(C_2H_4O)_mCH_3$, $CH_3OCOO(C_3H_6O)_n(C_2H_4O)_mC_3H_7$, and $C_2H_5OCOO\ (C_3H_6O)_n(C_2H_4O)_mC_2H_5$ wherein each of n and m represents an integer of 0–100 with the proviso that n+m=1 to 100.

12. The lubricating oil of claim 11 wherein the mixing weight ratio between the polycarbonate of formula (II) and the monocarbonate of formula (XXX) is in the range of from 75/25 to 20/80.

* * * * *